(12) United States Patent
Yang et al.

(10) Patent No.: US 6,992,764 B1
(45) Date of Patent: Jan. 31, 2006

(54) MEASURING AN ALIGNMENT TARGET WITH A SINGLE POLARIZATION STATE

(75) Inventors: Weidong Yang, Milpitas, CA (US); Roger R. Lowe-Webb, Sunnyvale, CA (US); Silvio J. Rabello, Palo Alto, CA (US); John D. Heaton, Fremont, CA (US)

(73) Assignee: Nanometrics Incorporated, Milpitas, CA (US)

( * ) Notice: Subject to any disclaimer, the term of this patent is extended or adjusted under 35 U.S.C. 154(b) by 419 days.

(21) Appl. No.: 10/261,547

(22) Filed: Sep. 30, 2002

(51) Int. Cl.
  *G01J 4/00* (2006.01)
(52) U.S. Cl. ............ 356/369; 356/400; 430/22
(58) Field of Classification Search ......... 356/369, 356/400, 364–368, 401; 430/22; 250/548, 250/491.1
See application file for complete search history.

(56) References Cited

U.S. PATENT DOCUMENTS

| | | | |
|---|---|---|---|
| 4,141,780 A | 2/1979 | Kleinknecht et al. | 156/626 |
| 4,172,664 A | 10/1979 | Charsky et al. | 356/356 |
| 4,408,884 A | 10/1983 | Kleinknecht et al. | 356/496 |
| 4,555,767 A | 11/1985 | Case et al. | 250/341.4 |
| 4,593,368 A | 6/1986 | Fridge et al. | 364/525 |
| 4,656,347 A * | 4/1987 | Une et al. | 250/548 |
| 4,672,196 A | 6/1987 | Canino | 250/225 |
| 4,707,610 A | 11/1987 | Lindow et al. | 250/560 |
| 4,748,335 A | 5/1988 | Lindow et al. | 250/572 |
| 5,007,708 A | 4/1991 | Gaylord et al. | 350/162.2 |
| 5,035,770 A | 7/1991 | Braun | 156/643 |
| 5,042,949 A | 8/1991 | Greenberg et al. | 356/345 |
| 5,042,951 A | 8/1991 | Gold et al. | 356/369 |
| 5,045,704 A | 9/1991 | Coates | 250/372 |
| 5,164,790 A | 11/1992 | McNeil et al. | 356/355 |
| 5,191,216 A | 3/1993 | Henderson et al. | 257/28 |
| 5,214,492 A | 5/1993 | LoBianco et al. | 356/400 |
| 5,216,257 A | 6/1993 | Brueck et al. | 250/548 |
| 5,216,680 A | 6/1993 | Magnusson et al. | 372/20 |
| 5,307,152 A | 4/1994 | Boehnlein et al. | 356/376 |

(Continued)

FOREIGN PATENT DOCUMENTS

EP  0 402 191 A1  12/1990

(Continued)

OTHER PUBLICATIONS

Bischoff, J. et al., "Light Diffraction Based Overlay Measurement" *Proceedings of SPIE*, vol. 4344 (2001) pp. 222-233.

(Continued)

*Primary Examiner*—Layla G. Lauchman
(74) *Attorney, Agent, or Firm*—Silicon Valley Patent Group LLP

(57) ABSTRACT

An alignment target includes periodic patterns on two elements. The periodic patterns are aligned when the two elements are properly aligned. By measuring the two periodic patterns with an incident beam having a single polarization state and detecting the intensity of the resulting polarized light, it can be determined if the two elements are aligned. The same polarization state may be detected as is incident or different polarization states may be used. A reference measurement location may be used that includes a third periodic pattern on the first element and a fourth periodic pattern on the second element, which have a designed in offset, i.e., an offset when there is an offset of a known magnitude when the first and second element are properly aligned. The reference measurement location is similarly measured with a single polarization state.

24 Claims, 12 Drawing Sheets

U.S. PATENT DOCUMENTS

| | | | |
|---|---|---|---|
| 5,337,146 A | 8/1994 | Azzam | 356/367 |
| 5,349,440 A | 9/1994 | DeGroot | 356/349 |
| 5,355,219 A * | 10/1994 | Araki et al. | 356/490 |
| RE34,783 E | 11/1994 | Coates | 250/372 |
| 5,363,171 A | 11/1994 | Mack | 355/68 |
| 5,555,474 A | 9/1996 | Ledger | 356/381 |
| 5,559,598 A | 9/1996 | Matsumoto | 356/490 |
| 5,559,601 A | 9/1996 | Gallatin et al. | 356/363 |
| 5,596,406 A | 1/1997 | Rosenewaig et al. | 356/327 |
| 5,596,413 A | 1/1997 | Stanton et al. | 356/401 |
| 5,607,800 A | 3/1997 | Ziger | 430/8 |
| 5,646,730 A | 7/1997 | Mitchell et al. | 356/356 |
| 5,739,909 A | 4/1998 | Blayo et al. | 356/369 |
| 5,747,813 A | 5/1998 | Norton et al. | 250/372 |
| 5,805,290 A | 9/1998 | Ausschnitt et al. | 356/401 |
| 5,808,742 A * | 9/1998 | Everett et al. | 356/509 |
| 5,841,139 A | 11/1998 | Sostek et al. | 250/339.12 |
| 5,867,276 A | 2/1999 | McNeil et al. | 356/445 |
| 5,880,838 A | 3/1999 | Marx et al. | 356/351 |
| 5,889,593 A | 3/1999 | Bareket | 356/445 |
| 5,900,633 A | 5/1999 | Solomon et al. | 250/339.08 |
| 5,963,329 A | 10/1999 | Conrad et al. | 356/372 |
| 5,969,819 A | 10/1999 | Wang | 356/371 |
| 6,031,614 A | 2/2000 | Michaelis et al. | 356/369 |
| 6,077,756 A | 6/2000 | Lin et al. | 438/401 |
| 6,079,256 A * | 6/2000 | Bareket | 73/105 |
| 6,084,712 A | 7/2000 | Harding | 359/618 |
| 6,097,488 A | 8/2000 | Grek et al. | 356/364 |
| 6,100,985 A | 8/2000 | Scheiner et al. | 356/381 |
| 6,130,750 A | 10/2000 | Ausschnitt et al. | 356/401 |
| 6,281,974 B1 | 8/2001 | Scheiner et al. | 356/381 |
| 6,366,861 B1 | 4/2002 | Waldhauer et al. | 702/35 |
| 6,407,396 B1 | 6/2002 | Mih et al. | 250/491.1 |
| 6,429,930 B1 | 8/2002 | Littaue et al. | 356/124 |
| 6,429,943 B1 | 8/2002 | Opsal et al. | 356/625 |
| 6,433,878 B1 | 8/2002 | Niu et al. | 356/603 |
| 6,458,605 B1 | 10/2002 | Stirton | 438/7 |
| 6,476,920 B1 | 11/2002 | Scheiner et al. | 356/630 |
| 6,483,580 B1 | 11/2002 | Xu et al. | 356/300 |
| 6,556,947 B1 | 4/2003 | Scheiner et al. | 702/172 |
| 6,699,624 B2 | 3/2004 | Niu et al. | 430/5 |
| 6,710,876 B1 | 3/2004 | Nikoonahad et al. | 356/401 |
| 6,804,005 B2 * | 10/2004 | Bischoff et al. | 356/369 |
| 2002/0018217 A1 | 2/2002 | Weber-Grabau et al. | 356/601 |
| 2002/0024669 A1 | 2/2002 | Danner et al. | 356/369 |
| 2002/0033945 A1 | 3/2002 | Xu et al. | 356/369 |
| 2002/0033954 A1 | 3/2002 | Niu et al. | 356/601 |
| 2002/0035455 A1 | 3/2002 | Niu et al. | 703/4 |
| 2002/0038196 A1 | 3/2002 | Johnson et al. | 702/179 |
| 2002/0051564 A1 | 5/2002 | Benesh et al. | 382/145 |
| 2002/0105646 A1 | 8/2002 | Zhao et al. | 356/369 |
| 2002/0113966 A1 | 8/2002 | Schegrov et al. | 356/369 |
| 2002/0135875 A1 | 9/2002 | Niu et al. | 359/564 |
| 2002/0149782 A1 | 10/2002 | Raymond | 356/616 |
| 2002/0158193 A1 | 10/2002 | Sezginer et al. | 250/237 |
| 2003/0002043 A1 | 1/2003 | Abdulhalim et al. | 356/400 |
| 2003/0020912 A1 | 1/2003 | Norton et al. | 356/369 |
| 2003/0042579 A1 | 3/2003 | Schulz | 257/629 |
| 2003/0043372 A1 | 3/2003 | Schulz | 356/327 |
| 2003/0043375 A1 | 3/2003 | Opsal | 356/369 |
| 2003/0044702 A1 | 3/2003 | Schulz | 430/30 |
| 2003/0160163 A1 | 8/2003 | Wong et al. | 250/237 |
| 2003/0169423 A1 | 9/2003 | Finarov et al. | 250/237 |
| 2003/0223630 A1 | 12/2003 | Adel et al. | 382/145 |
| 2004/0101983 A1 | 5/2004 | Jones et al. | 438/14 |

FOREIGN PATENT DOCUMENTS

| | | |
|---|---|---|
| EP | 0 402 191 B1 | 12/1990 |
| EP | 0 601 580 A1 | 6/1994 |
| EP | 1 037 012 A1 | 9/2000 |
| JP | 0225038 | 12/1984 |
| JP | 11-211421 | 8/1999 |
| JP | 11-211422 | 8/1999 |
| SU | 1747877 A1 | 7/1992 |
| WO | WO 99/45340 | 9/1999 |
| WO | WO 01/84382 A1 | 11/2001 |
| WO | WO 02/25723 A2 | 3/2002 |
| WO | WO 02/27288 A1 | 4/2002 |
| WO | WO 02/50501 A1 | 6/2002 |
| WO | WO 02/065545 A2 | 8/2002 |
| WO | WO 02/069390 A2 | 9/2002 |
| WO | WO 02-079760 A2 | 10/2002 |
| WO | WO 02/084213 A1 | 10/2002 |
| WO | WO 03/071471 A1 | 8/2003 |
| WO | WO 2004/008068 A1 | 1/2004 |

OTHER PUBLICATIONS

Michaelis, A. et al., "Spectroscopic Anistropy Micro-Ellipsometry (SAME) for determiation of lateral and vertical dimensions of sub-micron lithographic structures" IEEE Catalog No. 99TH8453 (1999) pp. 131-134.

NanoWave:Technology/development tools, http://www.nanowave.com/technology applications/tech devtoolsPR.html, 2 pages, downloaded Apr. 9, 2002.

NanoWave:Technology/how it works, http://www.nanowave.com/technology applications/tech HIWPR.html, 3 pages, downloaded Apr. 9, 2002.

NanoWave:Technology/product design, http://www.nanowave.com/technology applications/tech designPR.html, 4 pages, downloaded Apr. 9, 2002.

"A Diffraction Grating Analysis Tool", downloaded May 7, 2001 from <http://www.gsolver.com/gsprod.html>, Grating Solve Development Co. (1999).

Ahmed, S., et al., "Comparison of beam propagation method and rigorous coupled-wave analysis for single and multiplexed volume gratings", Applied Optics, vol. 35, No. 22, Aug. 1, 1996, pp. 4426-4435.

Allgair, J. et al., "Implementation of Spectroscopic Critical Dimension (SCDTM) for Gate CD Control and Stepper Characterization", *Proceedings of SPIE* vol. 4344 (2001), pp. 462-471.

Azzam, R. et al., "Ellipsometry And Polarized Light" *Elsevier Science Publishers* (1977, 1987) pp. 476-481.

Bao, G. et al., "Mathematical studies in rigorous grating theory", *J. Opt. Soc. Am. A*, vol. 12, No. 5 (1995), pp. 1029-1042.

Bao, G. et al., "Modeling and Optimal Design of Diffractive Optical Structures", pp. 1-27. (The correct site is Survey on Industrial Math. 8 (1998), 37-62).

Benson, T. et al., "In-situ Spectroscopic Reflectometry for Polycrystalline Silicon Thin Film Etch Rate Determination During Reactive Ion Etching", Dept. of Electrical Engineering & Computer Science an the Center for Display Technology & Manfuacturing, University of Michigan, pp. 1-34.

Bischoff J. et al., "Modeling of optical scatterometry with finite-number-of-periods gratings", *SPIE* vol. 3743 (1999) pp. 41-46.

Bischoff, J. et al., "Single feature metrology by means of light scatter analysis", *SPIE* vol. 3050 (1997) pp. 574-589.

Bishop, K. P. et al., "Grating line shape characterization using scatterometry", *SPIE*, vol. 1545 (1991) pp. 64-73.

Bishop, K. P. et al., "Use of scatterometry for resist process control", *Proc. SPIE—Int. Soc. Opt. Eng.*, vol. 1673 (1992) pp. 441-452.

Bosenberg, W. et al., "Linewidth Measurement on IC Wafers by Diffraction from Grating Test Patterns", *Solid State Technology*, vol. 26, No. 7 (1983) pp. 79-85.

Brauer, R. et al., "Eletromagnetic diffraction analysis of two-dimensional gratings", Optics Communications, vol. 100 (1993) pp. 1-5.

Chang, N. Y., et al., "Algorithm based on rigorous coupled-wave analysis for diffractive optical element design", J. Opt. Soc. Am. A, Opt. Image Sci. Vis. (USA), vol. 18, No. 10, Oct. 2001, pp. 2491-2501.

Chateau, N. et al., "Algorithm for the rigorous coupled-wave analysis of grating diffraction, " J. Opt. Soc. Am. A, vol. 11 (1994), pp. 1321-1331.

Corle, T., et al., "Polarization-enhanced imaging of photoresist gratings in the real-time scanning optical microscope", Applied Optics, vol. 33, No. 4 (1994) pp. 670-677.

Coulombe, S. A. et al., "Modal characteristics of short-pitch photoresist gratings exhibiting zero-order diffraction anomalies", J. Opt. Soc. Am. A, vol. 16, No. 12 (Dec. 1999), pp. 2904-2913.

Coulombe, S. A. et al., "Scatterometry measurement of sub-0.1 $\mu$m linewidth gratings", J. Vac. Sci. Technol.. B, vol. 16, No. 1 (1998) pp. 80-87.

Coulombe, S. et al., "Ellipsometric-Scatterometry for sub-01. mm CD measurements" SPIE vol. 3332 (1988) pp. 282-292.

Damar, H. et al., "Diffraction Characterization for Process Monitoring, Linewidth Measurement and Alignment" SPIE vol. 470 (1984) pp. 157-163.

Davidson, M. et al., "A comparison between rigorous light scattering methods", SPIE vol. 3051 (1997) pp. 606-619.

Dong Hoon Lee, et al., "Analysis of topological effects of phase-shifting mask by boundary element method", J. Inst. Electron. Eng. Korea D (South Korea), vol. 36-D, No. 11, Nov. 1999, pp. 33-44.

Galarza, C. et al., "Real-time Estimation of Patterned Wafer Parameters Using In Situ Spectroscopic Ellipsometry", Proceedings of the IEEE (1999) pp. 773-778.

Gaspar, S. M. et al., "Laser scatterometry for process characterization", AIP Conference Proceedings, vol. 227, No. 1, (1991) pp. 54-55.

Gaylord, T. et al., "Analysis and Applications of Optical Diffraction by Gratings," Proceedings of the IEEE, vol. 73, (1984), pp. 894-937 (1985).

Glytsis, E. et al., "Rigorous Coupled-Wave Analysis And Applications Of Grating Diffraction", Critical Reviews Of Optical Science and Technology, vol. CR49 (1993), pp. 1-31.

Glytsis, E. et al., "Three-dimensional (vector) rigorous coupled-wave analysis of anisotropic grating diffraction", J. Opt. Soc. Am. A, vol. 7, No. 8 (1990), pp. 1399-1420.

Glytsis, E. N. et al., "Review of rigorous coupled-wave analysis and of homogeneous effective medium approximations for high spatial-frequency surface-relief", In NASA. Marshall Space Flight Center, Conference on Binary Optics: An Opportunity for Technical Exchange Feb. 23-25, 1993, p 61-76.

Han, Chang-Wook, et al., "Rigorous coupled-wave analysis of antireflective surface-relief gratings" J. Opt. Soc. Korea (South Korea) vol. 1, Mar. 1997, pp. 26-35.

Han, S. et al., "Electromagnetic scattering of two-dimensional surface-relief dielectric grating", Applied Optics, vol. 31 (1992) pp. 2343-2352.

Hatab, Ziad R. et al., "Sixteen-megabit dynamic random access memory trench depth characterization using two-dimensional diffraction analysis", J. Vac. Sci. Technol. B, vol. 13, No. 2 (1995) pp. 174-182.

Hauge, P., "Recent Developments in Instrumentation in Ellipsometry", Surface Science 96, (1980) pp. 108-140.

Haverlag, M. et al., "In situ ellipsometry and reflectometry during etching of patterned surfaces: Experiments and simulations", Journal of Vacuum Science & Technology B, vol. 10, No. 6 (1992) pp. 2412-2418.

Heimann, P. et al., "Optical Etch-Rate Monitoring: Computer Simulation of Reflectance", Journal Electrochem. Soc., vol. 131, No. 4 (1984) pp. 881-885.

Henderson, G. N., "Semiconductor quantum electron wave transport, diffraction, and interference: analysis, device, and measurement", Dissertation Georgia Institute of Technology, vol. 54-10B, 1993, pp. 5312 209 page(s).

Hickman, K. C. et al., "Use of diffracted light from latent images to improve lithography control", J. Vac. Sci. & Tech. B, vol. 10, No. 5 (1992) pp. 2259-2266.

Huang, H. et al., "Normal-incidence spectroscopic ellipsometry for critical dimension monitoring", Applied Physics Letters, vol. 78 (2001) pp. 3983-3985.

Jarem, J. M., "Rigorous coupled wave analysis of radially and azimuthally-inhom- ogeneous, elliptical, cylindrical systems" (Abstract), J. Electromagn. Waves Appl. (Netherlands), vol. 15, No. 10, 2001, pp. 1367-1368.

Jarem, J. M., et al., "Rigorous coupled-wave analysis of photorefractive reflection gratings", J. Opt. Soc. Am. B, Opt. Phys. (USA) vol. 15, No. 7, Jul. 1998, pp. 2099-2106.

Jarem, J.M. "A rigorous coupled-wave analysis and crossed-diffraction grating analysis of radiation and scattering from three-dimensional inhomogeneous objects" IEEE Transactions on Antennas and Propagation, vol. 46, No. 5, May 1998, p. 740, 741.

Jiang Yongyuan, et al., Rigorous coupled wave analysis of dynamic diffraction properties of photorefractive phase grating Acta Photonica Sin. (China) vol. 29, No. 3, Mar. 2000, pp. 216-222.

Jiang Yongyuan, et al., "Rigorous coupled wave analysis of dynamic property of photorefractive anisotropic self-diffraction" Acta Photonica Sin. (China), vol. 29, No. 9, Sep. 2000, pp. 787-790.

Kamiya, N., "Rigorous coupled-wave analysis for practical planar dielectric gratings. 2. Diffraction by a surface-eroded hologram layer" Appl. Opt. (USA) vol. 37, No. 25, Sep. 1, 1998, pp. 5854-5863.

Kamiya, N., "Rigorous coupled-wave analysis for practical planar dielectric gratings. 3. Increase of higher-order lights owing to degenerated complex diffraction" Appl. Opt. (USA), vol. 37, No. 25, Sep. 1, 1998, pp. 5864-5878.

Kamiya, N., "Rigorous coupled-wave analysis for practical planar dielectric gratings. 1. Thickness-changed holograms and some characteristics of diffraction efficiency", Appl. Opt. (USA) vol. 37, No. 25, Sep. 1, 1998, pp. 5843-5853.

Kleinknecht, H. et al., "Linewidth measurement on IC masks and wafers by grating test patterns", Applied Optics, vol. 19, No. 4 (1980) pp. 525-533.

Kong, W. et al., "A Hybrid Analysis Ellipsometry Data from Patterned Structures" Characterization and Metrology for ULSI Technology: 2000 International Conference, pp. 373-377 (2001).

Kong, W. et al., "Analysis of Time-Evolved Spectroscopic Ellipsometry Data from Patterned Structures for Etching Process Monitoring and Control", Dept. of Electrical Engineering and Computer Science, University of Michigan, Four pages.

Kong, W., "Analysis of Spectroscopic Ellipsometry from Patterned Structures for Etching Process Monitoring and Control", Dissertation University of Michigan, 2001, 141 page(s).

Konstastantinos P. et al., "Use of Light Scattering in Characterizing Reactively Ion Etched Profiles", ATT&T Bell Laboratories, Murray Hill, NJ 07974, Page No. and date unavailable; Also cited in NAN007 RX as Giapis, K. et al., "Use of Light Scattering in Characterizing Reactively Ion Etched Profiles", J. Vac. Sci. Technol. A, vol. 9 (1981), pp. 664-668.

Krukar, R. et al., Overlay and Grating Line Shape Metrology Using Optical Scatterometry (unclassifed) DARPA I 1993 Final Report, (Oct. 11, 1993) Thirty-six pages.

Krukar, R. et al., "Reactive ion etching profile and depth characterization using statistical and neural network analysis of light scattering data", *J. Appl. Phys.*, vol. 74, No. 6 (1993) pp. 3698-3706.

Krukar, R. H. et al., "Analyzing simulated and measured optical scatter for semiconductor process verification", *Proc. SPIE—Int. Soc. Opt. Eng.*, vol. 1907 (1993) pp. 238-249.

Krukar, R. H. et al., "Using scattered light modeling for semiconductor critical dimension metrology and calibration", *Proc. SPIE—Int. Soc. Opt. Eng.*, vol. 1926 (1993) pp. 60-71.

Krukar, R. H. et al., "Wafer examination and critical dimension estimation using scattered light" *Proc. SPIE—Int. Soc. Opt. Eng.*, vol. 1661 (1992) pp. 323-332.

Lee, M. et al., "Analysis of Reflectometry and Ellipsometry Data from Patterned Structures", *Characterization and Metrology for ULSI Technology*, (1998) pp. 331-334.

Lee, S. G., et al., "More stable algorithm for rigorous coupled wave analysis applied to topography simulation in optical lithography and its numerical implementation", Proc. SPIE—Int. Soc. Opt. Eng. (USA), vol. 2726, 1996, pp. 288-298.

Lochbihler, H. et al., "Characterization of highly conducting wire gratings using an electromagnetic theory of diffraction" *Optics Communications* 100 (1993) pp. 231-239.

Lochbihler, H. et al., "Charactization of x-ray transmission gratings" *Applied Optics*, vol. 31 (1992) pp. 964-971.

Logofatu, P. C. et al. "Identity of the cross-reflection coefficients for symmetric surface-relief gratings", *J. Opt. Soc. Am. A, Opt* vol. 16 No. 5 (May 1999) pp. 1108-1114.

Logofatu, P. C. et al. "Measurement precision of optical scatterometry", *Proceedings of SPIE* vol. 4344 (2001), pp. 447-453.

Logofatu, P. C. et al. "Scatterometry: a metrology for subwavelength surface relief gratings", *Proceedings of SPIE*, vol. 4344 (2001), pp. 472-483.

Logofatu, P. C. et al., "Sensitivity analysis of fitting for scatterometry", *Proc. SPIE—Int. Soc. Opt. Eng.*; vol. 3677 (1999) pp. 177-183.

Logofatu, P.C., "Sensitivity-optimized scatterometry", Dissertation The University of New Mexico, vol. 61-11B, 2000, pp. 5942 181 page(s).

Lopez, A. G. "Reformulation of the rigorous coupled-wave analysis (RCWA) equations: Photonic crystals applications" Dissertation, Cornell University, vol. 61-04B, 2000, pp. 2113 136 pages.

Marx, D. et al., "Polarization quadrature measurement of subwavelength diffracting structures", *Applied Optics*, vol. 36, No. 25 (1997), pp. 6434-6440.

McNeil, J. R. "Application of optical scatterometry to microelectronics processing", *Technical Digest. Summaries of Papers Presented at the Conference on Lasers and Electro-Optics.*, vol. 6 (1998) pp. 348-349.

McNeil, J. R. et al., "Scatterometry applied to microelectronics processing", *Solid State Technol.*, vol. 36, No. 3 (1993) pp. 29-30.

McNeil, J. R., et al., "Scatterometry applied to microelectronics processing" *Solid State Technol.* vol. 36, No. 4 (1993) pp. 53-56.

McNeil, J. R., "Instrumentation to Enhance Optical Scatterometry for Semiconductor Metrology Development", Final Rept. Sep. 1, 1993-Feb. 28, 1998, Contract No. F49620-93-1-0512, Defense Technical Information Center (DTIC) order No.- AD-A354-189 (1998) (23 pages).

McNeill, J. et al., "Scatterometry Applied to Microelectronics Processing" *Microlithography World* (1992) pp. 16-22.

Mills, D. et al., "Spectral ellipsometry on patterned wafers," *SPIE*, vol. 2637 (1995) pp. 194-203.

Milner, L. M et a., "Latent image exposure monitor using scatterometry", *SPIE Proceedings* vol. 1673 (1992), 10 pages.

Milner, L. M. et al., "Lithography process monitor using light diffracted from a latent image", *Proc. SPIE—Int. Soc. Opt. Eng.*, vol. 1926 (1993) pp. 94-105.

Minhas, B. K. et al., "Ellipsometric scatterometry for the metrology of sub-0.1-$\mu$m-linewidth structures", *Applied Optics*, vol. 37 No. 22 (Aug., 1998) pp. 5112-5115.

Minhas, B. K. et al., "Towards sub-0.1 mu m CD measurements using scatterometry", *Proc. SPIE—Int. Soc. Opt. Eng.*, vol. 2725 (1996) pp. 729-739.

Moharam, M. et al., "Diffraction analysis of dielectric surface-relief gratings", *J. Opt. Soc. Am.*, vol. 72 (1982) pp. 1385-1392.

Moharam, M. et al., "Diffraction characteristics of photoresist surface-relief gratings" *Applied Optics*, vol. 23 (1984) pp. 3214-3220.

Moharam, M. et al., "Formulation for stable and efficient implementation of the rigorous coupled-wave analysis of binary gratings", *J. Opt. Soc. Am.*, vol. 12 (1995) pp. 1068-1076.

Moharam, M. et al., "Rigorous coupled-wave analysis of planar-grating diffraction", *J. Opt. Soc. Am* vol. 71, No. 7 (1981) pp. 811-818.

Moharam, M. et al., "Stable implementation of the rigorous coupled-wave analysis for surface-relief gratings: enhanced transmittance matrix approach", *J. Opt. Soc Am.*, vol. 12 (1995) pp. 1077-1086.

Moharam, M. et al., "Three-dimensional vector coupled-wave analysis of planar-grating diffraction", *J. Opt. Soc. Am.*, vol. 73, No. 9 (1983), pp. 1105-1112.

Moharam, M., "Coupled-Wave Analysis of Two-Dimensional Dielectric Gratings", *SPIE* vol. 883 (1988) pp. 8-11.

Moharam, M.G. et al. "Rigorous Coupled-Wave Analysis of Grating Diffraction- E-mode polarization and losses", Jnl. of the Optical Society of America, vol. 73, No. 4, Apr. 1983, p451-455.

Moharam, M.G. et al, "Rigorous coupled-wave analysis of metallic surface-relief gratings" Optical Society of America, Journal, A: Optics and Image Science Optical Society of America, Journal, A: Optics and Image Science, vol. 3, Nov. 1986, p. 1780-1787.

Murnane, M. R. et al., "Scatterometry for 0.24-0.70 um developed photoresist metrology", *SPIE*, vol. 2439 (1995) pp. 427-436.

Murnane, M. R. et al., "Subwavelength photoresist grating metrology using scatterometry", *Proc. SPIE—Int. Soc. Opt. Eng.*, vol. 2532 (1995) pp. 251-261.

Nakagawa, W., et al., "Analysis of near-field effects in artifical dielectric structures using rigorous coupled-wave analysis", Conference Proceedings—Lasers and Electro-Optics Society Annual Meeting-LEOS, vol. 2, 1999, p 495-496.

Nakagawa, W., et al., "Ultrashort pulse propagation in near-field periodic diffractive structures by use of rigorous coupled-wave analysis", J. Opt. Soc. Am. A, Opt. Image Sci. Vis. (USA), vol. 18, No. 5, May 2001, pp. 1072-1081.

Naqvi, S. S. H. et al., "Etch depth estimation of large-period silicon gratings with multivariate calibration of rigorously simulated diffraction profiles", *J. Opt. Soc. Am. A*, vol. 11, No. 9 (1994) pp. 2485-2493.

Naqvi, S. S. H., et al., "Optical scatterometry for process metrology", *Optical metrology; Proceedings of the Conference*, (Jul. 1999) pp. 129-144.

Niu, X., et al., "Specular Spectroscopic Scatterometry", IEEE Transactions on Semiconductor Manufacturing, vol. 14, No. 2, May 2001, pp. 97-111.

Peng, Song, et al., "Efficient and stable implementation of rigorous coupled-wave analysis for surface-relief gratings", Proc. SPIE—Int. Soc. Opt. Eng. (USA), vol. 2532, 1995, pp. 475-480.

Peng, Song, et al., "Efficient implementation of rigorous coupled-wave analysis for surface-relief gratings", Journal of the Optical Society of America A: Optics and Image Science, and Vision, vol. 12, No. 5, May 1995-1087-1096.

Press, W. et al., "Numerical Recipes: The Art of Scientific Computing,", *Cambridge University Press*, Section 14.4 (1986), pp. 521-528.

Prins, S. L. et al., "Scatterometric sensor for PEB process control", *Proc. SPIE—Int. Soc. Opt. Eng.*, vol. 2725 (1996) pp. 710-719.

Raymond, C. et al., "Metrology of subwavelength photoresist gratings using optical scatterometry" *J. Vac. Sci. Technology. B* 13 (1995) pp. 1484-1495.

Raymond, C. et al., "Resist and etched line profile characterization using scatterometry" *SPIE* vol. 3050 (1977) 476-486.

Raymond, C. et al., "Scatterometry for the measurement of metal features" *Proceedings of SPIE* vol. 2998 (2000) pp. 135-146.

Raymond, C. J. et al., "Multiparameter CD measurements using scatterometry", *Proc. SPIE—Int. Soc. Opt. Eng.*, vol. 2725 (1996) pp. 698-709.

Raymond, C. J. et al., "Multiparameter grating metrology using optical scatterometry" *J. of Vac. Sci. Tech. B*, vol. 15, No. 2 (1997) pp. 361-368.

Raymond, C. J. et al., "Multi-parameter process metrology using scatterometry", *Proc. SPIE—Int. Soc. Opt. Eng.*, vol. 2638 (1995) pp. 84-93.

Raymond, C. J. et al., "Resist and Etched line profile characterization using scatterometry", *Proc. SPIE—Int. Soc. Opt. Eng.*, vol. 3050 (1997) pp. 476-486.

Raymond, C. J. et al., "Scatterometry for CD measurements of etched structures", *Proc. SPIE—Int. Soc. Opt. Eng.*, vol. 2725 (1996) pp. 720-728.

Sohail, S. "A simple technique for linewidth measurement of gratings on photomasks", *Proc. SPIE—Int. Soc. Opt. Eng.*, vol. 1261 (1990) pp. 495-504.

Sohail, S. et al. "Grating parameter estimation using scatterometry" *Proc. SPIE—Int.Soc. Opt. Eng.*, vol. 1992 (1993) pp. 170-80.

Sohail, S. et al., "Diffractive techniques for lithographic process monitoring and control ", *J. Vac. Sci. Technol. B*, vol. 12, No. 6 (1994) pp. 3600-3606.

Sohail, S. et al., "Linewidth measurement of gratings on photomasks: a simple technique", *Applied Optics*, vol. 31, No. 10 (1992) pp. 1377-1384.

Stover, J. C., et al., "Modeled and measured scatter from vias", SPIE Conf on Surface Characterization of Computer Disks, Wafers, and Flat Panel Displays, Jan. 1999, pp. 65-71.

Sun, J. et al., "Profile Measurement on IC Wafers by Holographic Interference", *SPIE* vol. 673 (1986) pp. 135-143.

Tadros, K., "Understanding metrology of polysilicon gates through reflectance measurements and simulation", *SPIE* vol. 1464 (1991) pp. 177-186.

Tu, K. et al., "Multiple-scattering theory of wave diffraction by superposed volume gratings", *J. Opt. Soc. Am. A.*, vol. 7, No. 8 (1990), pp. 1421-1435.

Wilson, S. M. G. et al., "Phase shift mask metrology using scatterometry", *Proc. SPIE—Int. Soc. Opt: Eng.*, vol. 2322 (1994) pp. 305-315.

Yeung, M., et al., "Electromagnetic Scatterometry Applied to In Situ Metrology", *Proceedings of SPIE*, vol. 4344 (2001), pp. 484-495.

Ziger, D. et al., "Linesize effects on ultraviolet reflectance spectra", *Society of Photo-Optical Instrumentation Engineers* (1997), Paper 37046.

Zylberberg, Z. et al., "Rigorous coupled-wave analysis of pure reflection gratings" Optical Society of America, Journal, vol. 73, Mar. 1983, p. 392-398.

D.C. Flanders & Henry I. Smith, A new interferometric alignment techniques), Applied Physics Letters, vol. 31, No. 7, Oct. 1 1997, pp. 426-428.

\* cited by examiner

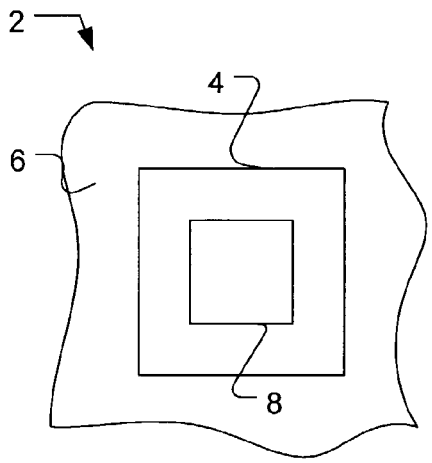
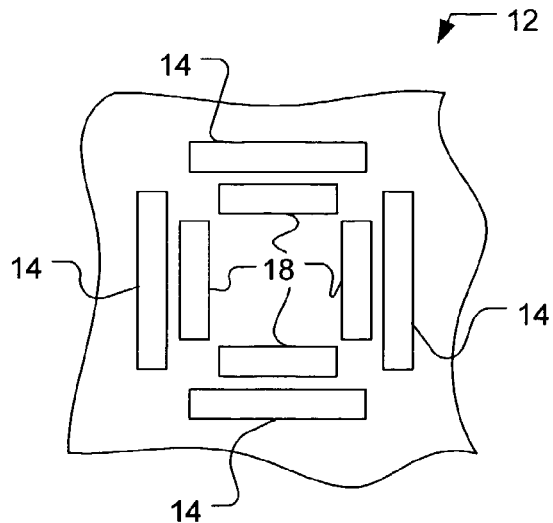
Fig. 1A
(Prior Art)
Fig. 1B
(Prior Art)
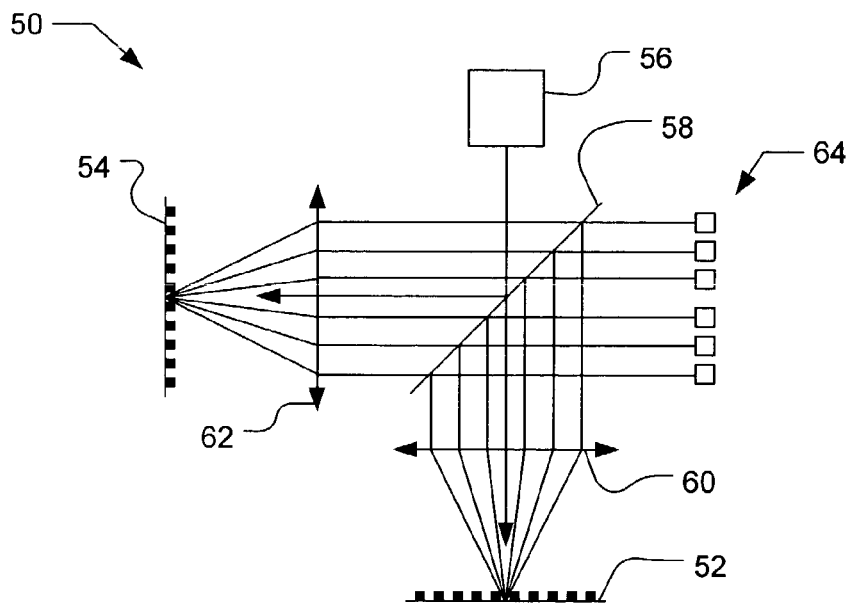
Fig. 2
(Prior Art)

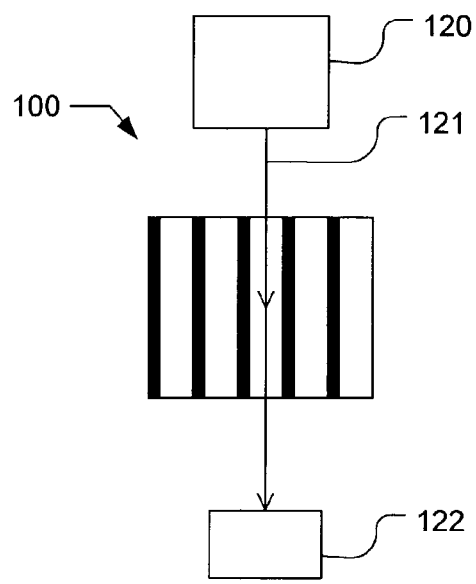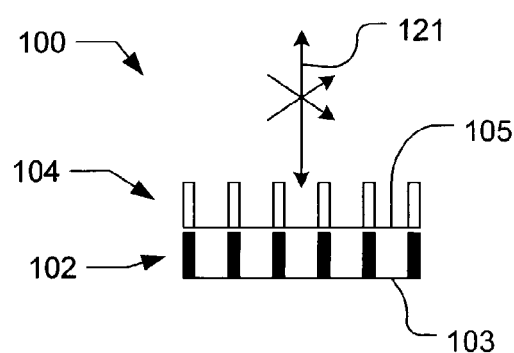
Fig. 3A          Fig. 3B
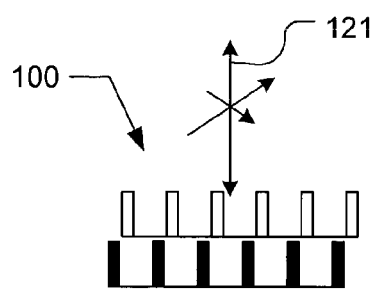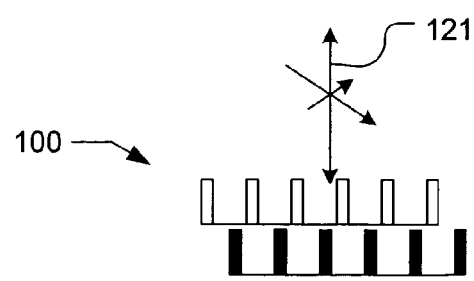
Fig. 4          Fig. 5

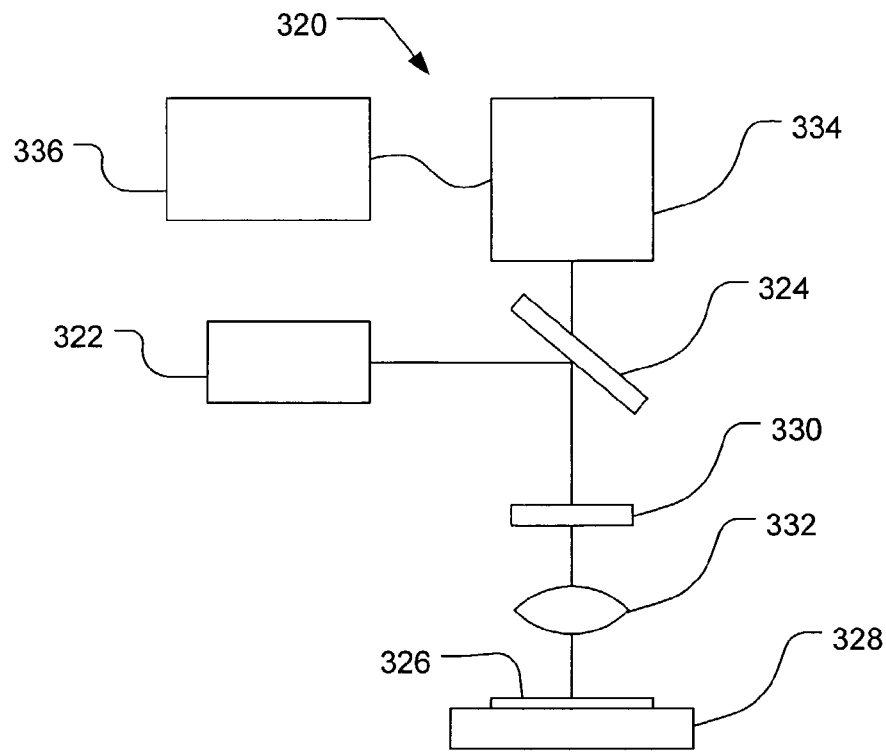
Fig. 8A
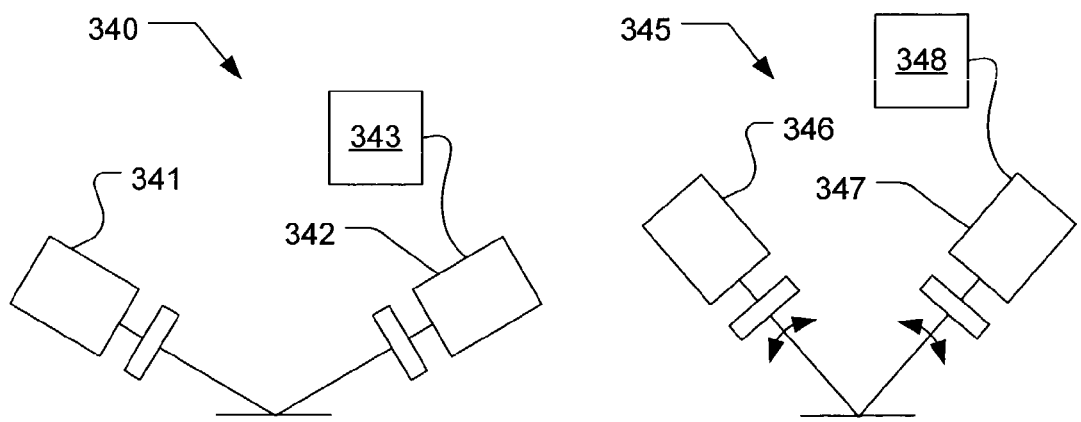
Fig. 8B
Fig. 8C

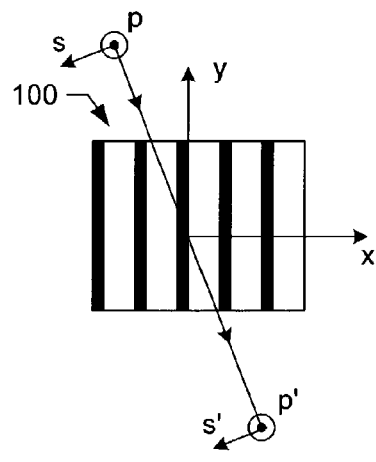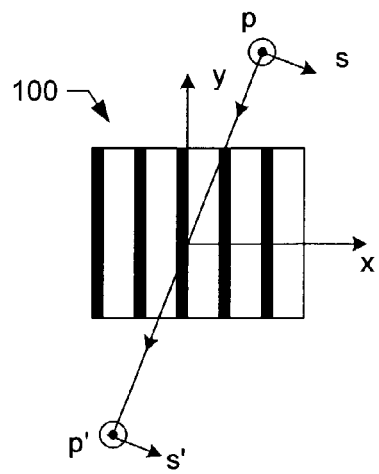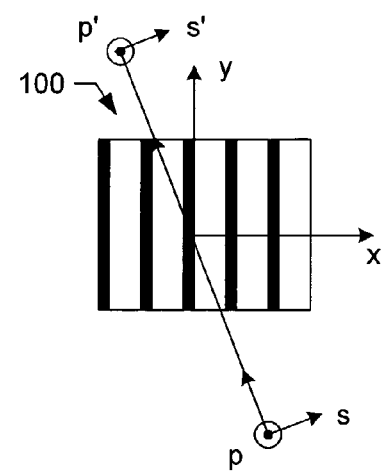
Fig. 9B  Fig. 9C  Fig. 9D
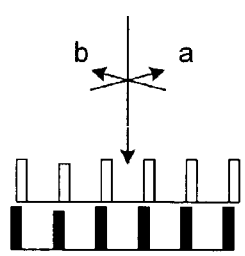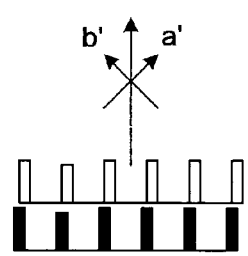
Fig. 9E  Fig. 9F

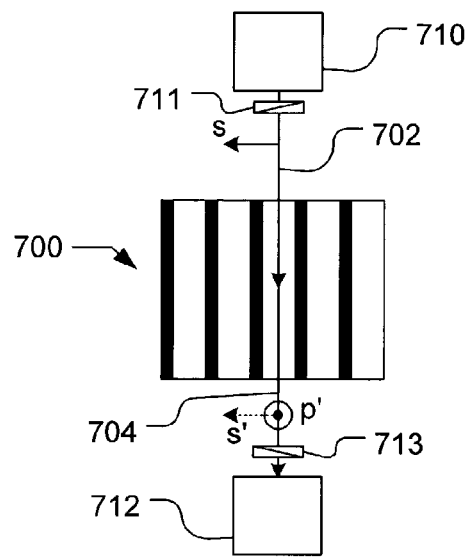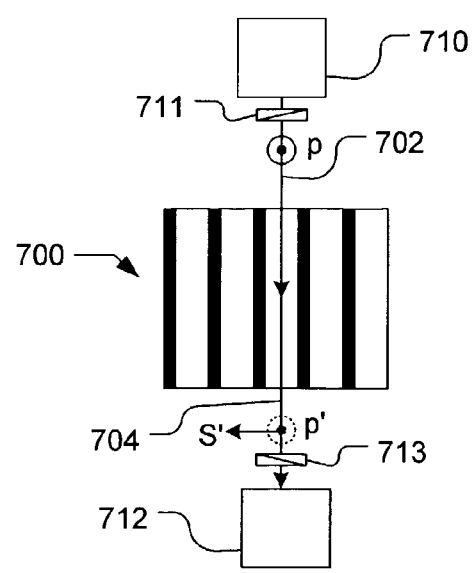
Fig. 14    Fig. 15
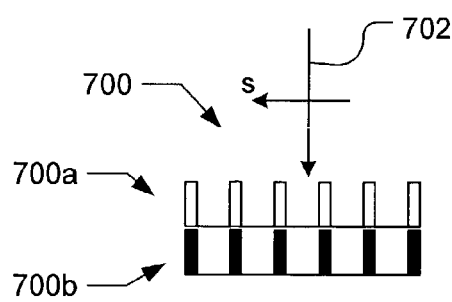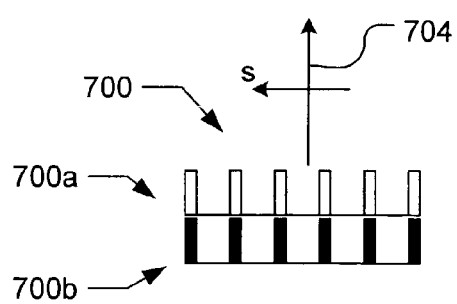
Fig. 16A    Fig. 16B
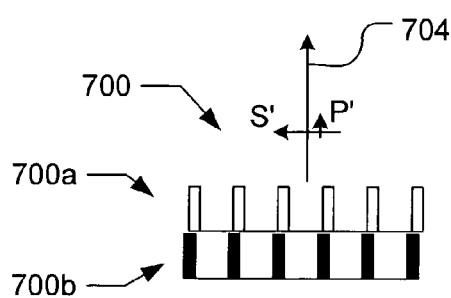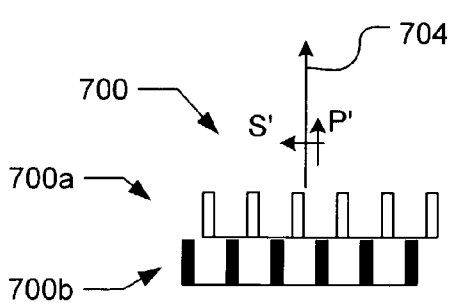
Fig. 17A    Fig. 17B

MEASURING AN ALIGNMENT TARGET WITH A SINGLE POLARIZATION STATE

BACKGROUND OF THE INVENTION

1. Field of the Invention

The present invention relates to alignment metrology, and in particular to an alignment target and method of use.

2. Discussion of the Related Art

Semiconductor processing for forming integrated circuits requires a series of processing steps. These processing steps include the deposition and patterning of material layers such as insulating layers, polysilicon layers, and metal layers. The material layers are typically patterned using a photoresist layer that is patterned over the material layer using a photomask or reticle. It is important that one layer is aligned with another during processing.

Typically, the photomask has alignment targets or keys that are aligned to fiduciary marks formed in the previous layer on the substrate. However, as the integrated circuit feature sizes continue to decrease to provide increasing circuit density, it becomes increasingly difficult to measure the alignment accuracy of one masking level to the previous level. This overlay metrology problem becomes particularly difficult at feature sizes below approximately 100 nm where overlay alignment tolerances are reduced to provide reliable semiconductor devices.

FIGS. 1A and 1B show conventional overlay targets used with conventional imaging metrology methods. FIG. 1A shows a typical Box-in-Box overlay target 2. Target 2 is formed by producing an etched box 4 in a material layer 6 on a substrate. A corresponding smaller box 8 on the photomask or reticle is aligned to the larger box 4 so that the centers of the large and small boxes are aligned.

FIG. 1B shows a Bar-in-Bar overlay target 12, which is similar to target 2 shown in FIG. 1A. Target 12 is produced by etching bars 14 in a material layer 16 on a substrate. The bars 18 on the photomask are aligned to the overlay target alignment bars 14.

After the smaller box 8 or bars 18 are developed, i.e., exposed and etched, the overlay target is imaged to determine whether the photomask or reticle was properly aligned with the underlying layer. Conventionally, high magnification imaging is used to measure overlay alignment. Conventional imaging devices, unfortunately, suffer from disadvantages such as sensitivity to vibration and cost. Moreover, conventional imaging devices suffer from a trade-off between depth-of-focus and optical resolution. Additionally, edge-detection algorithms used to analyze images for the purpose of extracting overlay error are inaccurate when the imaged target is inherently low-contrast or when the target suffers from asymmetries due to wafer processing.

During processing, the substrate is moved from one location to the next so that different areas, e.g., dies, on the substrate can be exposed. The alignment system, e.g., the exposure tool, typically uses an alignment target to properly align the substrate during exposure. FIG. 2 shows a conventional alignment system 50, which includes a diffraction pattern 52 on the substrate and a second diffraction pattern 54 that is stationary, e.g., is fixed to the lens on the exposure tool. A light source 56 produces coherent light that passes through a beam splitter 58 and is incident on the diffraction pattern 52 after passing through a lens 60. The light is diffracted by diffraction pattern 52 and passes through lens 60 back to beam splitter 58. The coherent light beam from source 56 is also reflected off beam splitter 58, passes through lens 62 and is incident on diffraction pattern 54. The light diffracted by diffraction pattern 54 passes back through lens 62 to beam splitter 58. At beam splitter the light diffracted from diffraction patterns 52 and 54 is combined and the combined diffraction light is received by light detectors 64.

Alignment system 50 provides an accuracy of approximately 15 nm. One disadvantage of alignment system 50 is that coherent light is used. Thus, if the diffraction pattern 52 on the sample absorbs the particular frequency used, alignment system 50 cannot provide an accurate measurement. While multiple coherent light sources may be used to avoid this disadvantage, the use of multiple light sources adds complexity and cost.

Thus, there is a need in the semiconductor industry for an improved alignment target for metrology and alignment system.

SUMMARY

An alignment target in accordance with the present invention is used to determine if two elements are in alignment or to determine the amount of the alignment error between the two elements. The alignment target includes periodic patterns on the two elements. The periodic patterns, which may be, e.g., diffractions gratings, are aligned when the two elements are in alignment. The alignment target is measured by producing light with a single polarization state. The polarization state of the incident light is perpendicular or parallel to the direction of periodicity of the alignment target. The intensity of the resulting light after interacting with the alignment target is then measured at a single polarization state that is perpendicular or parallel to the polarization state of the incident light. The polarized resulting light will be periodic as a function of relative position of the two elements. The periodicity of the resulting light can be used to determine when the first element and the second element are aligned.

In one embodiment, a method includes providing an alignment target on a first element and a second element, the alignment target having a first periodic pattern on the first element and a second periodic pattern on the second element. The first and second periodic patterns are illuminated with incident light having a first polarization state. The light interacts with the first and second periodic patterns and the resulting light is polarized. The polarized resulting light is then detected. The alignment of the first element and the second element is then determined based on the detected polarized resulting light. The resulting light may be polarized parallel or perpendicular to the polarization state of the incident light. Moreover, the polarization state of the incident light may be parallel or perpendicular to the periodicity of the first and second alignment targets. One or both of the periodic patterns may be diffraction gratings having periodicities in one or two directions. The method may include moving one element with respect to the other while detecting the polarized resulting light. Because the intensity of the polarized resulting light is periodic, it can be determined when the two elements are aligned.

The alignment target may further include a third periodic pattern on the first element and a fourth periodic pattern on the second element, the third periodic pattern and the fourth periodic pattern have a designed in offset of a known magnitude such that when the first element and second element are aligned, the third periodic pattern and the fourth periodic pattern are offset by the known magnitude. The third and fourth periodic patterns are illuminated with incident light with a single polarization state. The resulting light is polarized and then detected. The alignment of the first and second elements can then be determined using the detected polarized light from the first and second periodic patterns and the detected polarized light from the third and fourth periodic patterns. The detected polarized light from the third and fourth periodic patterns can be used as a reference for detected polarized light from the first and second periodic patterns.

In another embodiment, an apparatus for determining the alignment of a first element with a second element using an alignment target having a first periodic pattern on the first element and a second periodic pattern on the second element, includes a light source for producing light having a first polarization state, the light is to be incident on the alignment target. The first polarization state may be perpendicular or parallel to the direction of periodicity of the first periodic pattern and the second periodic pattern. The apparatus further includes a polarizing element for polarizing the light after interacting with the alignment target and a detector for detecting the resulting polarized light. The polarizing element polarizes the light with a polarization state that is perpendicular or parallel to the polarization state of the incident light. The apparatus may include a processor to determine when the alignment target is aligned based on the detected resulting polarized light. The apparatus may further include a stage controlled by the processor, the stage moving the first element with respect to the second element to align the first element and the second element.

BRIEF DESCRIPTION OF THE DRAWINGS

FIGS. 1A and 1B show conventional overlay targets used with conventional imaging metrology methods.

FIG. 2 shows a conventional alignment system, which includes a diffraction pattern on the substrate and a second diffraction pattern that is stationary, e.g., is fixed to the lens on the exposure tool.

FIGS. 3A and 3B show top and cross-sectional views, respectively, of an alignment target in accordance with an embodiment of the present invention.

FIGS. 4 and 5 show the alignment target in accordance with the present invention with an alignment error.

FIGS. 8A, 8B, 8C show metrology devices that may be used to measure the diffraction from an alignment target in accordance with the present invention.

FIGS. 9A, 9B, 9C, 9D, 9E, and 9F show the alignment target being measured from different angles simultaneously.

FIG. 14 shows a top view of an alignment target being illuminated by a single state s type polarization beam and with the resulting p polarized light is detected.

FIG. 15 shows a top view of an alignment target being illuminated by a single state p type polarization beam and with the resulting s polarized light is detected.

FIGS. 16A and 16B show side views of an alignment target with the top and bottom periodic patterns in alignment and with an incident beam and a resulting beam, respectively.

FIGS. 17A and 17B show side views of an alignment target with the top and bottom periodic patterns out of alignment and the polarization states of the resulting beams.

DETAILED DESCRIPTION

Figure 6:
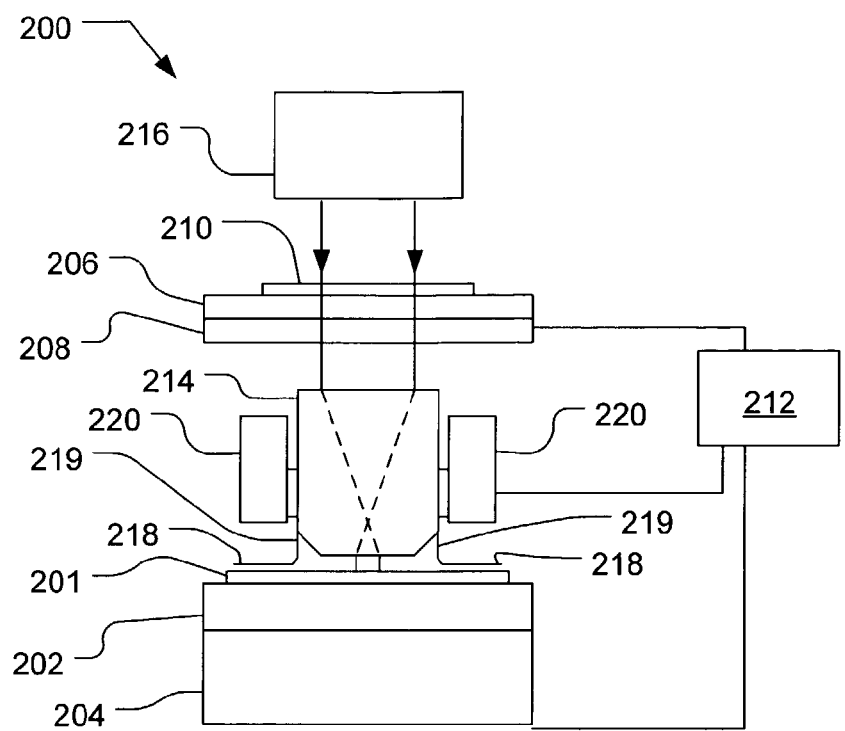
FIG. 6 is a block diagram of an alignment system with which the alignment target may be used.

An alignment target is measured using a single polarization state, in accordance with the present invention, to align two elements. For example, the alignment target can be used to align a substrate and/or a reticle with respect to a stationary element, e.g., the lens, in an exposure tool. Of course, the alignment target is not limited to use in an exposure tool, but may be used to align any two elements. Additionally, the alignment target can be used to measure the amount of alignment error between any two elements, such as two layers on a substrate or any other elements. An alignment target suitable for use with the present invention is described in U.S. patent application "Measuring An Alignment Target with Multiple Polarization States" by Weidong Yang and Roger R. Lowe-Webb, Ser. No. 10/116, 798, filed Apr. 4, 2002, and which has the same assignee as the present application and is incorporated herein by reference.

The alignment target and method of use of the present invention is similar to the alignment target used to assist in the alignment process and to measure alignment error as described in U.S. patent applications "Positioning Two Elements Using an Alignment Target With A Designed In Offset" by Weidong Yang, Roger R. Lowe-Webb, John D. Heaton and Guoguang Li, Ser. No. 10/116,964; "Alignment Target with Designed in Offset" by Weidong Yang, Roger R. Lowe-Webb, and John D. Heaton, Ser. No. 10/116,863; and "Encoder with Alignment Target", by Weidong Yang, Roger R. Lowe-Webb, and John D. Heaton, Ser. No. 10/116,855, all of which were filed on Apr. 4, 2002, and have the same assignee as the present application and are incorporated herein by reference.

FIGS. 3A and 3B show top and cross-sectional views, respectively, of an alignment target 100 that may be used with an embodiment of the present invention. Alignment target 100 includes a periodic pattern 102 on a first element 103 and another periodic pattern 104 on a second element 105. The periodic patterns 102, 104, which may be diffraction gratings, are designed to be in alignment with respect to each other when layers 103 and 105 are in alignment. The first element 103 and second element 105 may be movable with respect to each other. For example, the first and second element 103 and 105 may be two stages or a substrate and/or reticle and another object, such as a lens or a reference mask coupled to a lens, in an exposure tool. The elements 103 and 105 may also be layers on a substrate, such as a semiconductor wafer, flat panel display or any other structure in which accurate alignment of successive layers is desired. The periodic patterns of alignment target 100 are similar to that described in U.S. Ser. No. 09/960,892 entitled "Spectroscopically Measured Overlay Target", filed Sep. 20, 2001, which has the same assignee as the present disclosure and which is incorporated herein in its entirety by reference.

The bottom periodic pattern 102 is produced, for example, by providing a layer of appropriate material, such as a 200 nm layer of polysilicon, followed by a layer of photoresist. The desired image including the periodic pattern 102 is exposed in the photoresist, which is then developed. The polysilicon is then etched away leaving periodic pattern 102.

The top periodic pattern 104 is produced using, e.g., photoresist, in a manner similar to the bottom periodic pattern 102. The top periodic pattern 104 may be separated from the bottom periodic pattern 102 by one or more intermediate layers. Thus, for example, an 800 nm layer of the photoresist may be used to produce top periodic pattern 104. The desired image including the periodic pattern is exposed in the photoresist layer. The photoresist may then be developed to produce periodic pattern 104, or alternatively, a latent image may be used as periodic pattern 104.

It should be understood that the processing steps used to produce periodic patterns 102 and 104 are exemplary. Different or additional layers may be included between substrate and the bottom periodic pattern 102 or between the bottom periodic pattern 102 and the top periodic pattern 104. In fact, if desired, the top periodic pattern 104 may be on the same layer as the bottom periodic pattern 102, in which case, top and bottom refers to the order in which the gratings are produced, i.e., the bottom periodic pattern being first and the top periodic pattern being second. Thus, the alignment target 100 may be used to ensure that a first pattern produced on a first layer on the substrate is aligned with a second pattern produced on the same layer on the substrate. Moreover, the alignment target 100 may be used with two elements that are not connected. Thus, for example, the top periodic pattern 104, and the bottom periodic pattern 102 may be separated by a small distance, e.g., up to approximately 50 $\mu$m or more.

The dimensions of the patterns and the thicknesses of the layers may be altered. For example, the bottom diffraction grating 102 need not extend to the top of element 105. It should be understood that the alignment target 100 may be produced using various materials and the dimensions optimized for the materials used. Thus, the dimensions of the alignment target 100 may be altered to maximize sensitivity based on the types of materials used.

To determine if the layers 103, 105 are in alignment, a radiation source 120, such as a broadband light source, produces radiation 121 that is incident on alignment target 100. Source 120 produces light that has a non-normal angle of incidence and has an azimuthal angle that is non-parallel with the direction of periodicity of the periodic patterns in alignment target 100, if the pattern has only one periodicity direction.

The radiation source 120 produces radiation 121 that has a plurality of polarization states, e.g., two polarization states, as illustrated in FIG. 3B. After the radiation interacts with alignment target 100, a detector 122 detects the radiation. The difference in intensity of the polarization states from alignment target 100 vary proportionally with the alignment error. When the elements 103 and 105 are in alignment, periodic patterns 102 and 104 will be in alignment. Consequently, the polarization states in the detected radiation will have equal intensity. However, if there is an alignment error between elements 103 and 105, periodic patterns 102 and 104 will be out of alignment, as illustrated in FIGS. 4 and 5. With the periodic patterns 102 and 104 out of alignment, the intensity of the detected polarization states will be unequal. Thus, by comparing the intensities of the detected polarization states from alignment target 100, it is possible to determine if elements 103 and 105 are in alignment.

The ability to determine if elements 103 and 105 are in alignment is particularly useful in an alignment system. Thus, for example, the present invention may be used to ensure substrate to reticle registration when the substrate is on the exposure tool during processing. The alignment target may be used to assist in the precise alignment of separate elements in any alignment system and is not limited to an exposure tool.

It should be understood that the present invention may be used in both reflection and transmission modes.

The present invention may be used to measure the alignment error down to a fraction of a nanometer, while the current industry standard is approximately 15 nm. Thus, the present invention provides a large improvement compared to current technology.

FIG. 6 is a block diagram of an alignment system with which the alignment target 100 may be used. The alignment system is an exposure tool 200 includes X and Y substrate stages 202 and 204 that hold the substrate 201. The exposure tool 200 also includes X and Y reticle stages 206 and 208 that hold the reticle 210. Exposure tool 200 may include two sets of stages, one set for large motions and another set for fine motions. For sake of simplicity, X and Y stages 202, 204, 206, and 208 may be used for both large motion and fine motion.

A control system 212 controls the motion of the stages. A lens 214 or other suitable optics is positioned between the substrate 201 and the reticle 210 and is used to focus light from light source 216 that is transmitted through reticle 210 onto substrate 201. The operation and control of exposure tools is well known in the art.

A reference mask 218 extends from the lens 214 by way of a low thermal expansion arm 219. The distance between the reference mask 218 and the substrate 201 should be small, e.g., between 1 and 10 $\mu$m. Spectrometers 220 are positioned above reference masks 218. As shown in FIG. 6, a plurality of reference masks 218 may be used, each having an associated spectrometer 220.

Figure 7:
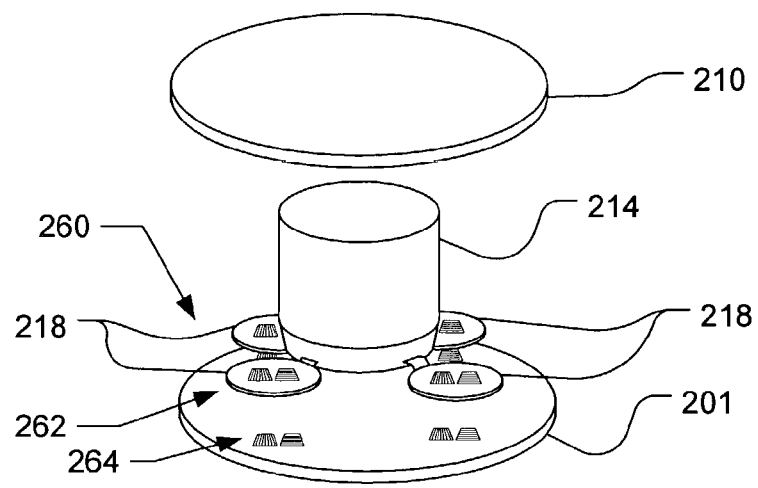
FIG. 7 shows a perspective view of a substrate and a reticle with a lens and four reference masks disposed between the substrate and reticle.

FIG. 7 shows a perspective view of substrate 201 and reticle 210 with lens 214 and four reference masks 218 disposed between the substrate 201 and reticle 210. The spectrometers 220 are not shown in FIG. 7. As can be seen in FIG. 7, a number of separate alignment targets are used, where the top periodic pattern 262 is on the reference masks 218 and bottom periodic pattern 264 is on the substrate 201.

Referring back to FIG. 6, the spectrometers 220 may be coupled to the lens 214 as shown in FIG. 6, or may be connected to another stationary object. The spectrometers 220 communicate with the control system 212. The control system 212 includes, e.g., a computer-usable medium having computer-readable program code embodied therein for causing the control system to calculate the difference between the diffracted light from the two locations and using the difference to determine if the first element and the second element are aligned. The control system 212 is coupled to the stage to adjust the location of the substrate 201 in response to the signals provided by spectrometer 220 until the starting position of the substrate 201 is precisely aligned with the lens 214. Once the substrate 201 is aligned, the control system 212 can move the stages to perform the desired exposure operation.

Alignment target 100 may be used to measure the amount of alignment error, e.g., using several types of metrology devices, e.g., such as that shown in FIGS. 8A, 8B, and 8C. FIG. 8A, for example, shows a block diagram of a normal incidence polarized reflectance spectrometer. Spectrometer 320 is discussed in detail in the U.S. patent application entitled "Apparatus and Method for the Measurement of Diffracting Structures," filed Sep. 25, 2000, having Ser. No. 09/670,000, and the U.S. patent application entitled "Measurement Of Diffracting Structures Using One-Half Of The Non-Zero Diffracted Orders" filed Apr. 27, 2000, having Ser. No. 09/844,559, both of which have the same assignee as the present disclosure and are incorporated herein by reference. Spectrometer 320 may use rigorous coupled wave analysis (RCWA) as described in Ser. No. 09/670,000, or folded rigorous coupled wave analysis as described in Ser. No. 09/844,559 to measure the alignment error from alignment target 100. In an alignment system, such as that shown in FIG. 6, however, a precise measurement is not necessary. Only a determination of whether the polarization states have the same intensity needs to be made in order to determine if the periodic patterns are in alignment.

As shown in FIG. 8A, spectrometer 320 includes a polychromatic light source 322 that generates a light beam that is partially reflected by beam splitter 324 along the optical axis. The light beam is directed towards a sample 326 having an alignment target, such as alignment target 100, to be measured. Sample 326 may be, e.g., a semiconductor wafer or flat panel display or any other substrate, and is supported by a stage 328, which may be a polar coordinate, i.e., R-θ, stage or an x-y translation stage. Spectrometer 320 includes a rotatable polarizer 330 and a lens 332 (or series of lenses) to polarize and focus the light beam onto the sample 326 at normal incidence. The beam is reflected off sample 326 and the reflected light is transmitted through lens 332 and polarizer 330. A portion of the reflected light is transmitted through beam splitter 324 and is received by a spectrophotometer 334. Spectrophotometer 334 is coupled to processor 336, which analyzes the data provided by spectrophotometer 334. Processor 336 is e.g., a computer with a computer and a computer-usable medium having computer-readable program code embodied therein for causing the computer to determine the overlay error based on the light that is diffracted from the alignment target. Thus, the computer-readable program code causes the computer to calculate the difference between the intensities of the polarization states from the alignment target and use the difference to determine if the alignment target is aligned. One of ordinary skill in the art can program code necessary to determine alignment in accordance with the present invention in view of the present disclosure. For more information on the general operation of a normal incidence polarized reflectance spectrometer, the reader is referred to Ser. Nos. 09/670,000 and 09/844,559, which are incorporated herein by reference.

If desired, other measurement devices may be used to measure alignment target 100 including ellipsometry and scatterometry. FIGS. 8B and 8C show block diagrams of a spectroscopic ellipsometer 340 and spectroscopic scatterometer 345. Ellipsometer 340 includes a broadband radiation source 341 and a spectrophotometer 342, which is connected to a processor 343. Spectroscopic scatterometer 345 includes a broadband radiation source 346 and a spectrophotometer 347, which is connected to a processor 348. As indicated by the arrows in FIG. 8C, one or both of broadband radiation source 346 and spectrophotometer 347 are adjustable to alter the angle of incidence. The operation of an ellipsometer 340 and spectroscopic scatterometer 345 is well known to those skilled in the art. Processor 343 and 348 may be similar to processor 336 shown in FIG. 8A.

It should also be understood, that the present invention may use a single wavelength, a plurality of discrete wavelengths, or a continuum of wavelengths.

Figure 9A:
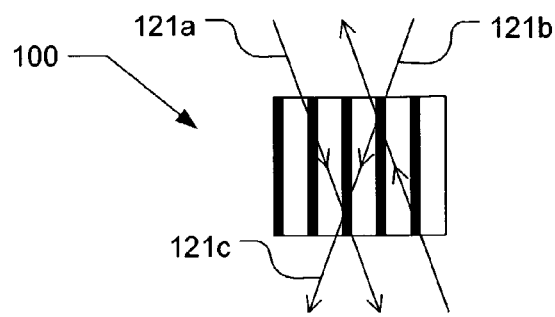

If desired, multiple light sources and detectors may be used simultaneously. FIG. 9A for example, shows alignment target 100 being measured from different angles simultaneously with a plurality of radiation beams, 121a, 121b, and 121c. Because of the symmetrical properties of the periodic patterns in alignment target 100, the measurement may be made at multiple symmetrical angles.

FIGS. 9B, 9C and 9D illustrate the symmetries of alignment target 100. As can be seen in FIGS. 9B, 9C, and 9D, alignment target 100 has mirror symmetry along the x-z plane, the y-z plane and 180 degree rotation symmetry around the z axis. The y-z plane mirror symmetry and z axis rotation symmetry are broken once the alignment pattern symmetry is broken, i.e., when there is an alignment error.

As illustrated in FIGS. 9B, 9C, and 9D, incident light has polarization components along s and p, with equivalent phase shifts shown in each figure. The light that is detected has polarization states s' and p' where there is also equivalent phase shifts shown in each figure. It should be understood that the phase shift in the incident light and the detected light need not be the same. Moreover, the polarization states need not be linear. Because of symmetry, the measurements in FIGS. 9C and 9D are identical and are also identical to the measurement in FIG. 9B, but only when the alignment patter is symmetrical. This difference can be used for alignment as well as shift measurement.

A special case is when the incident light comes in from the y direction, i.e., parallel to the lines, as shown in FIGS. 9E and 9F. In FIG. 9E, a and b represent the polarization states of the incident light for two measurements that follow the same light path and in FIG. 9F, a' and b' represent the polarization states of the resulting light for the two measurements. As can be seen, the two incidence polarization states (a and b) and the two detection polarization states (a' and b') mirror each other in the y-z plane. However, as can be seen, the polarization angles used in the incident light need not be used in the detection, i.e., a' and b' may differ from a and b, but should be symmetrical about the y-z plane.

It should be understood that multiple polarization states may be used to determine when the symmetry in the alignment target is broken. For example, in one embodiment, white light may be used to determine when the symmetry is broken.

In a special case, the polarization states of the two beams may overlap in either the incident beam or in the detection of the resulting beam.

The present invention may be used to not only determine if the elements are aligned, but to measure the alignment error if any. The alignment error may be measured using alignment target 100, for example, using a modeling technique, such as RCWA. Alternatively, a reference pattern may be used.

To measure the alignment error using a modeling technique, a model of the alignment target and the incident and diffracted light is produced. The modeled light is compared to the measured light to determine if there is an acceptable fit, i.e., the difference between the modeled light and measured light is within a specified tolerance. If an acceptable fit is not found, the alignment target and incident and diffracted light are remodeled and compared to the measured light. Once an acceptable fit between the measured and modeled light is found, it is known that the modeled alignment target accurately describes the actual alignment target. If desired, the difference in the spectra from the two polarization states may be determined before or after the comparison with the modeled light. Of course, if the difference in measured spectra is used, the model light must be the difference in the modeled spectra. Moreover, a number of models of the alignment target, including the modeled light, may be generated a priori and stored in a library.

Figure 10:
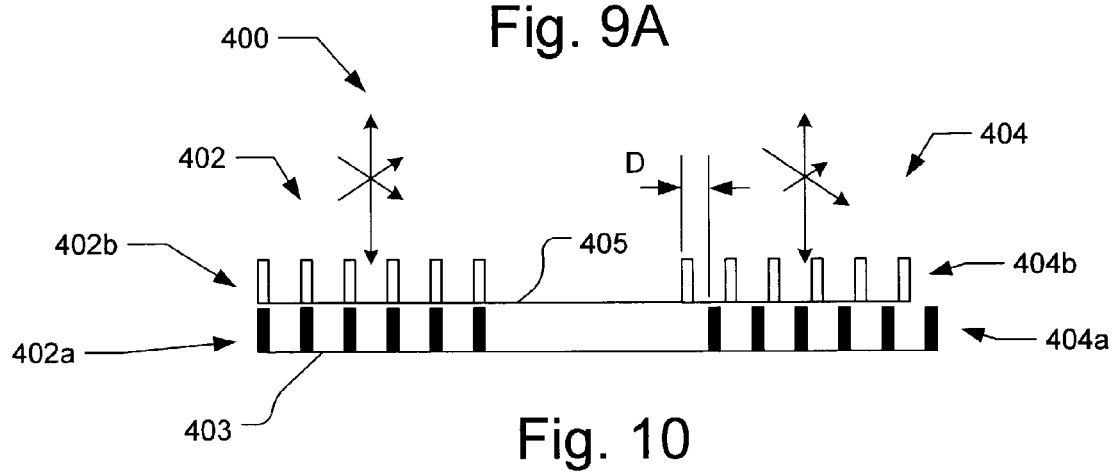
FIGS. 10 and 11 show a cross-sectional and top view, respectively, of an alignment target in accordance with another embodiment of the present invention.

FIG. 10 shows a cross-sectional view of an alignment target 400 in accordance with another embodiment of the present invention. Alignment target 400 includes two measurement locations, referred to as overlay patterns 402 and 404. Each of the overlay patterns 402, 404 includes a periodic pattern (402a, 404a) on a first element 403 and a periodic pattern (402b, 404b) on a second element 405. The overlay pattern 402 has no designed in offset, i.e., periodic patterns 402a and 402b are aligned when elements 403 and 405 are in proper alignment. Overlay pattern 404, however, has a designed in offset between the bottom periodic pattern 404a and 404b of a magnitude D.

It should be understood that periodic patterns 402b and 404b or periodic patterns 402a and 404a may be a part of the same continuous periodic pattern. Because the measurement is made at different locations, however, it is unimportant if the patterns are connected or not.

Figure 11:

FIG. 11 shows a top view of alignment target 400. The periodic patterns in overlay patterns 402 and 404 may be oriented at any non-perpendicular angle with respect to each other.

In operation, overlay pattern 404 is used as a reference pattern for alignment target 400. Each measurement location, i.e., overlay patterns 402 and 404, of alignment target 400 is measured at a plurality of, e.g., two, polarization states. When elements 403 and 405 are properly aligned, the intensities of the polarization states from overlay pattern 402 will be equal, but the intensities of the polarization states from overlay pattern 404 will be unequal. When there is an alignment error between the elements 403 and 405, the intensities of the polarization states from overlay pattern 402 will be unequal. Because the difference in the intensities of the polarization states varies proportionally with the alignment error, the difference in intensities of the polarization states from overlay pattern 404 may be used as a reference measurement.

In general, the alignment error e is determined by:

$$e = \frac{\varphi_1}{\varphi_2 - \varphi_1} * D \qquad \text{eq. 1}$$

wherein $\varphi_1$ is the differential spectra at the target location, i.e., overlay pattern 402, $\varphi_2$ is the differential spectra at the reference location, i.e., overlay pattern 404, and D is the designed in offset at the reference location. By fitting the alignment error e for the entire spectrum, the alignment error is determined as:

$$e = \frac{\sum_i \varphi_{1,i} * (\varphi_2 - \varphi_1)_i}{\sum_i (\varphi_2 - \varphi_1)_i^2} * D \qquad \text{eq. 2}$$

where i is the wavelength number in the spectrum. Further, if desired, a select portion of the full spectrum may be used to provide an optimized result. The portion of the full spectrum to be used may be determined by examining the wavelength dependent signal response to the alignment error either empirically or by modeling.

In another embodiment, the reference location is produced by moving the second element 405 with respect to the first element 403 by a distance D and measuring the pattern in the new position. In this embodiment, the second overlay pattern 404 is not necessary.

When the relationship between the differential spectra and the alignment error is assumed to be a polynomial, the higher orders can be treated by using additional reference patterns. The use of additional reference patterns and a polynomial equation to solve for the alignment error is discussed in more detail in U.S. patent application entitled "Alignment Target with Designed in Offset" by Weidong Yang, Roger R. Lowe-Webb, John D. Heaton, and Guoguang Li, which is incorporated herein.

Figure 12:
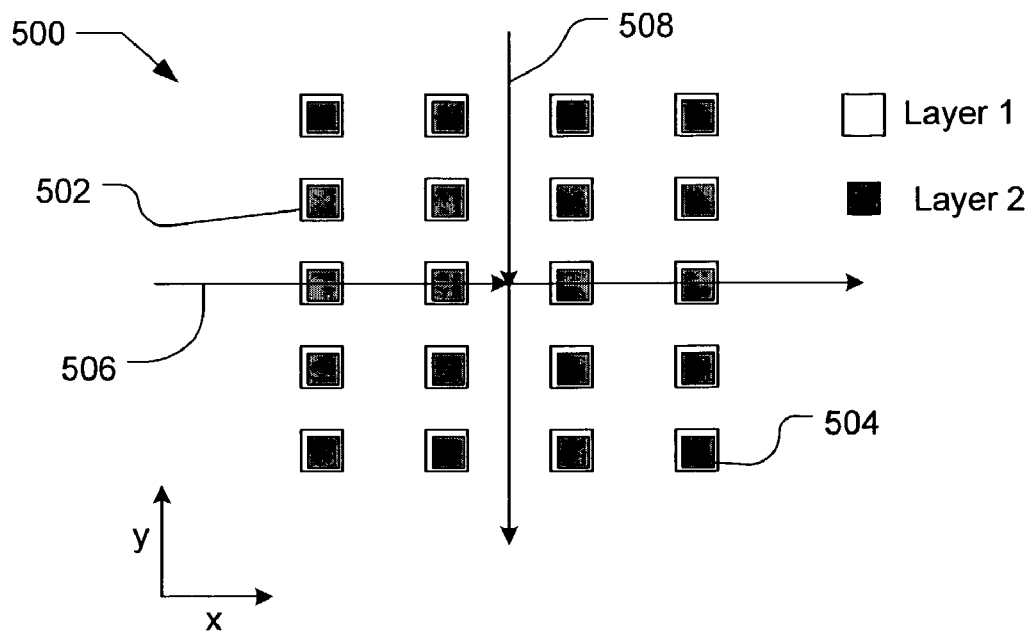
FIG. 12 shows top view of an alignment target in accordance with another embodiment of the present invention.

FIG. 12 shows top view of an alignment target 500 in accordance with another embodiment of the present invention. Alignment target 500 is a bi-grating includes two periodic patterns, a bottom periodic pattern 502, shown as solid squares, and a top periodic pattern 504, shown as empty squares that have periodicities in two directions. The two periodicities need not be perpendicular and the shapes forming the periodic patterns need not be square. Because the alignment target 500 has two periodicities, it can be used to determine alignment in two directions, shown as the X and Y direction in FIG. 12. Alignment target 500 is measured from two separate directions by beam 506, which is sensitive to alignment error in the Y direction and beam 508, which is sensitive to alignment error in the X direction.

Moreover, it should be understood that one or both of the periodic patterns, e.g., alignment target 100 in FIGS. 3A, 3B, can be a bi-grating if desired.

Figure 13:
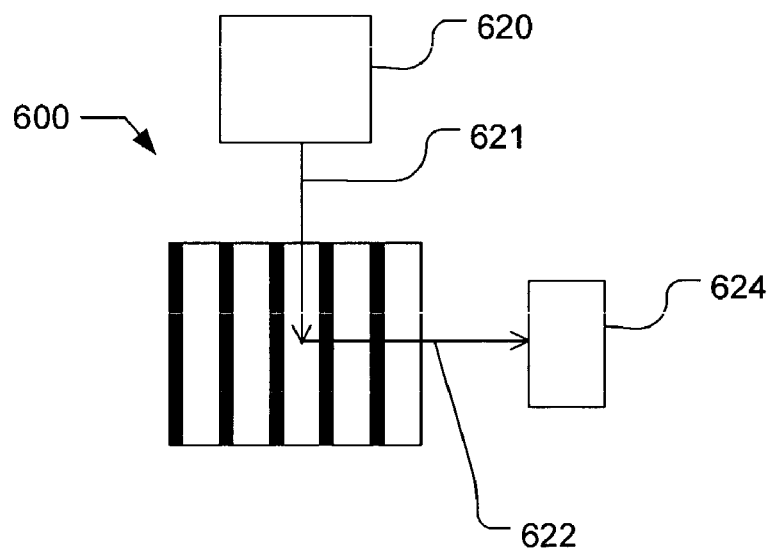
FIG. 13 shows measuring non-zero order diffracted light from an alignment mark.

Further, if desired, the incident light and the detected light need not share the same azimuthal angle. Thus, as shown in FIG. 13, an alignment mark 600, which is similar to alignment mark 100, may be measured by a light source 620 that produces an incident light beam 621 and a detector 624 that detects non-zero order diffracted light 622.

In general, the cross-reflection symmetry may be used for the error measurement and alignment control. The reflection of the light from a surface can be expressed as:

$$E_{out} = R \cdot E_{in} \qquad \text{eq. 3}$$

$$\text{where} \quad E = \begin{pmatrix} E_s \\ E_p \end{pmatrix} \qquad \text{eq. 4}$$

$$\text{and} \quad R = \begin{bmatrix} r_{pp} & r_{sp} \\ r_{ps} & r_{ss} \end{bmatrix} \qquad \text{eq. 5}$$

$r_{sp}$ and $r_{ps}$ are defined as the cross-reflection coefficients. For symmetric grating, the $0^{th}$ order cross-reflection coefficients are known to be identical but with a sign change in conical mount. With symmetry broken, they no longer have identical magnitude. This property can be exploited for alignment control and overlay error measurement.

In conical incidence, if the grating is symmetrical, $0^{th}$ orders are antisymmetrical, $r_{sp} = -r_{ps} \neq 0$, while the higher orders are symmetrical, $r_{sp} = r_{ps}$. For transmission, this relationship is reversed. The $0^{th}$ orders are symmetrical, while higher orders are antisymmetrical. Assume incidence light has polarization along angle $\theta_1$, with phase different $\phi_1$ between s and p polarizations. Also assume that the $0^{th}$ order refection is detected at polarization along angle $\theta_2$, with phase different $\phi_2$ between s and p polarizations. Incidence light can be described as:

$$E_{in} = \begin{pmatrix} E_s \\ E_p \end{pmatrix} = \begin{pmatrix} \sin(\theta_1) \\ \cos(\theta_1)e^{i\phi_1} \end{pmatrix} \qquad \text{eq. 6}$$

$0^{th}$ order reflection:

$$E_{out} = R \cdot E_{in} = \begin{bmatrix} r_{pp} & r_{sp} \\ r_{ps} & r_{ss} \end{bmatrix} \cdot \begin{pmatrix} \sin(\theta_1) \\ \cos(\theta_1)e^{i\phi_1} \end{pmatrix} = \qquad \text{eq. 7}$$

$$\begin{pmatrix} r_{pp}\sin(\theta_1) + r_{sp}\cos(\theta_1)e^{i\phi_1} \\ r_{ps}\sin(\theta_1) + r_{ss}\cos(\theta_1)e^{i\phi_1} \end{pmatrix}$$

The measured electric field is:

$$E_{measure} = (\sin(\theta_2)\cos(\theta_2)e^{i\phi_2}) \cdot E_{out} = \qquad \text{eq. 8}$$

$$(\sin(\theta_2)\cos(\theta_2)e^{i\phi_2}) \cdot \begin{pmatrix} r_{pp}\sin(\theta_1) + r_{sp}\cos(\theta_1)e^{i\phi_1} \\ r_{ps}\sin(\theta_1) + r_{ss}\cos(\theta_1)e^{i\phi_1} \end{pmatrix} =$$

$$r_{pp}\sin(\theta_1)\sin(\theta_2) + r_{ss}\cos(\theta_1)\cos(\theta_2)e^{i(\phi_1+\phi_2)} +$$

$$r_{sp}\sin(\theta_2)\cos(\theta_1)e^{i\phi_1} + r_{sp}\cos(\theta_2)\sin(\theta_1)e^{i\phi_2}$$

A second measurement is made along the same light path. Assume the incidence light has polarization along angle $\theta_2$, with phase different $\phi_1'$ between s and p polarizations. Also assume that the $0^{th}$ order refection is detected at polarization along angle $\theta_1$, with phase different $\phi_2'$ between s and p polarizations. The measured electric field is:

$$E_{measure} = (\sin(\theta_1)\cos(\theta_1)e^{i\phi_2'}) \cdot \begin{bmatrix} r_{pp} & r_{sp} \\ r_{ps} & r_{ss} \end{bmatrix} \cdot \begin{pmatrix} \sin(\theta_2) \\ \cos(\theta_2)e^{i\phi_1'} \end{pmatrix} = \qquad \text{eq. 9}$$

$$r_{pp}\sin(\theta_1)\sin(\theta_2) + r_{ss}\cos(\theta_1)\cos(\theta_2)e^{i(\phi_1'+\phi_2')} +$$

$$r_{sp}\sin(\theta_1)\cos(\theta_2)e^{i\phi_1'} + r_{sp}\cos(\theta_1)\sin(\theta_2)e^{i\phi_2'}$$

To obtain symmetrical measurements for symmetrical grating using symmetrical reflection or transmission orders, i.e. $r_{sp}=r_{ps}$, or $t_{sp}=t_{ps}$, the following condition has to be satisfied:

$$e^{i(\phi_1+\phi_2)}=e^{i(\phi_1'+\phi_2')}$$

$$e^{i\phi_1}=e^{i\phi_1'}$$

$$e^{i\phi_2}=e^{i\phi_2'} \qquad \text{eq. (10)}$$

which can be simplified as:

$$\phi_1=\phi_1'$$

$$\phi_2=\phi_2' \qquad \text{eq. (11)}$$

To obtain symmetrical measurements for symmetrical grating using antisymmetrical reflection or transmission orders, i.e. $r_{sp}=-r_{ps}$, or $t_{sp}=-t_{ps}$, the following condition has to be satisfied:

$$e^{i(\phi_1+\phi_2)}=e^{i(\phi_1'+\phi_2')}$$

$$e^{i\phi_1}=e^{i\phi_1'}$$

$$e^{i\phi_2}=e^{i\phi_2'} \qquad \text{eq. (10)}$$

Some special cases for antisymmetrical orders are as follows:
1) First and second incidence lights have polarization which is mirror symmetrical to s direction linear or non-linear, as does the first and second detection polarization, linear or non-linear.
2) First and second incidence lights have polarization which is mirror symmetrical to p direction linear or non-linear, as does the first and second detection polarization, linear or non-linear.
3) One of the polarization directions is s or p.
4) One of the polarization directions is s, the other is p. Effectively, one measurement is done with incidence polarization of p and detection polarization of s, the other is reversed.

It should be understood that the incidence paths for the two measurements do not need to be along the same path. The incidence paths could be mirror symmetry pair of x-z plane, where x is the grating vector direction.

In another embodiment of the present invention, a single polarization state is used to determine the alignment between a top periodic pattern and a bottom periodic pattern. FIG. 14 shows a top view of an alignment target 700, which is similar to alignment target 100 shown in FIGS. 3A and 3B, being illuminated by a single state polarization beam. As shown in FIG. 14, the incident beam 702 is produced by source 710, which includes polarizer 711 to produce a single polarization state, e.g., s polarization. The beam 702 is incident on alignment target 700 with an azimuthal angle that is parallel with the lines in the periodic pattern of the alignment target 700. The polarization state of the incident beam 702, thus, may be parallel to or perpendicular to the direction of periodicity in the alignment target 700. It should be understood that the alignment target may have periodicities in two directions. e.g., as shown in FIG. 12.

The intensity of the resulting light with a polarization state perpendicular or parallel to the polarization state of the incident beam is then detected. FIG. 14 shows the intensity of p' type polarized light in the resulting beam 704 (where the prime notation is used to indicate that it is the polarization state of the resulting beam 704) being detected by detector 712, which includes a polarizer 713 to select the p type polarized light. If desired, however, a parallel polarization state, i.e., s' polarized light, may be detected, as indicated by the broken line in FIG. 14. Alternatively, as shown in FIG. 15, the incident beam may have a polarization state of p, and the detector 712 receives the s' polarization state of the resulting beam 704 by way of polarizer 713. Again, if desired, a parallel polarization state, i.e., p' polarized light, may be detected, as indicated by the broken circle in FIG. 15. Based on the intensity of the polarization state of the resulting beam 704, the alignment between the top periodic pattern and the bottom periodic pattern may be determined.

FIG. 16A shows a side view of alignment target 700 with an incident beam 702 having a single polarization state, i.e., s type. FIG. 16B shows the resulting beam 704 from alignment target 700. When the top and bottom periodic patterns 700*a* and 700*b* are in alignment, as shown in FIGS.

16A and 16B, the polarization state of the resulting beam 704 will be the same as the polarization state of the incident beam 702. Consequently, the measured intensity of the p type polarized light in the resulting beam 704 will be approximately zero.

FIG. 17A shows a side view of alignment target 700 with the top and bottom periodic patterns 700a and 700b slightly out of alignment. As shown in FIG. 17A, the resulting beam 704 has both an s' type component and a p' type component. Consequently, the measured intensity of the p type polarized light in the resulting beam 704 will be non-zero. FIG. 17B is another view of alignment target 700 with the top and bottom periodic patterns 700a and 700b more out of alignment than shown in FIG. 17A. As shown in FIG. 17B, the resulting light 704 has an increased p' type component, and a decreased s' type component. Consequently, the measured intensity of the p type polarized light in the resulting beam 704 shown in FIG. 17B is greater than that measured in FIG. 17A.

Figure 18:
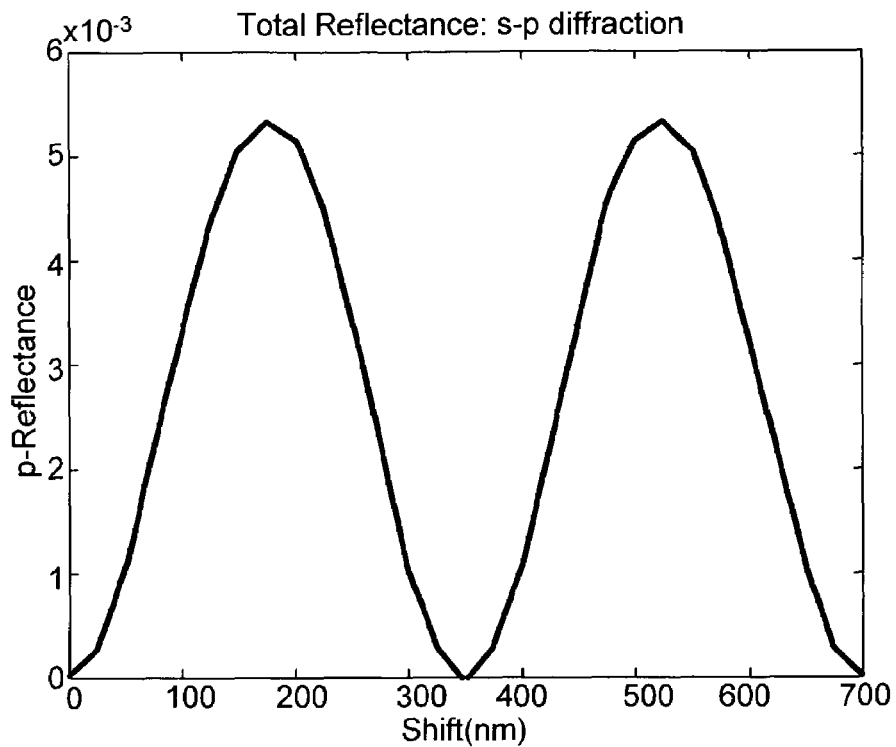
FIGS. 18, 19, and 20 show graphs of reflected light as a function of shift between the top and bottom periodic patterns, where the light is obliquely incident on the alignment target.
Figure 19:
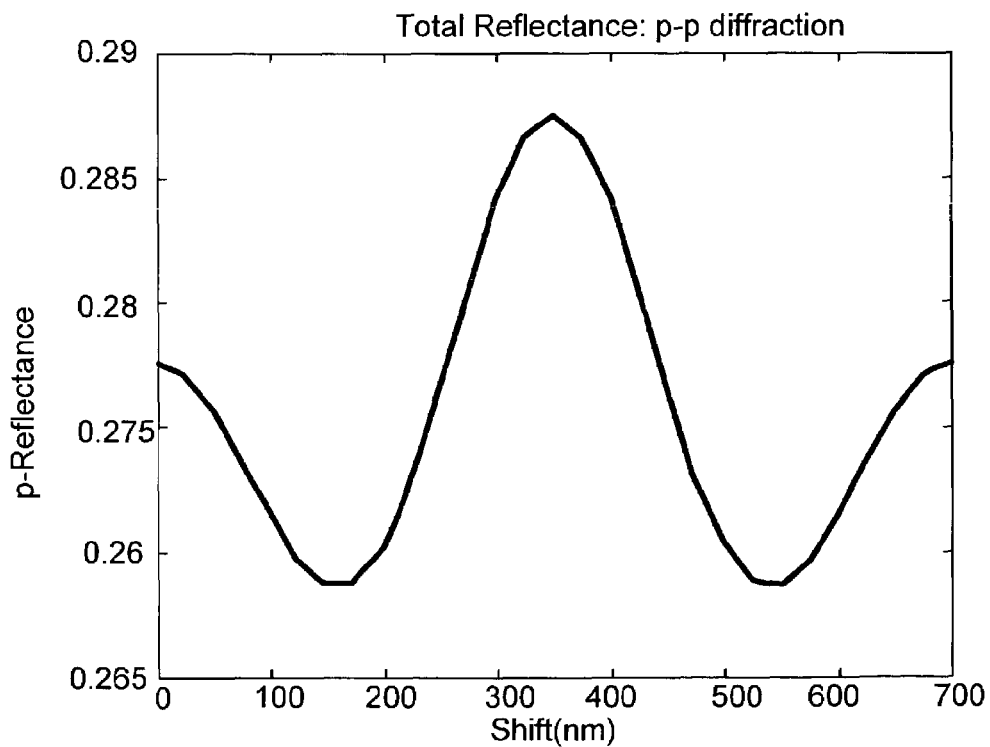
Figure 20:
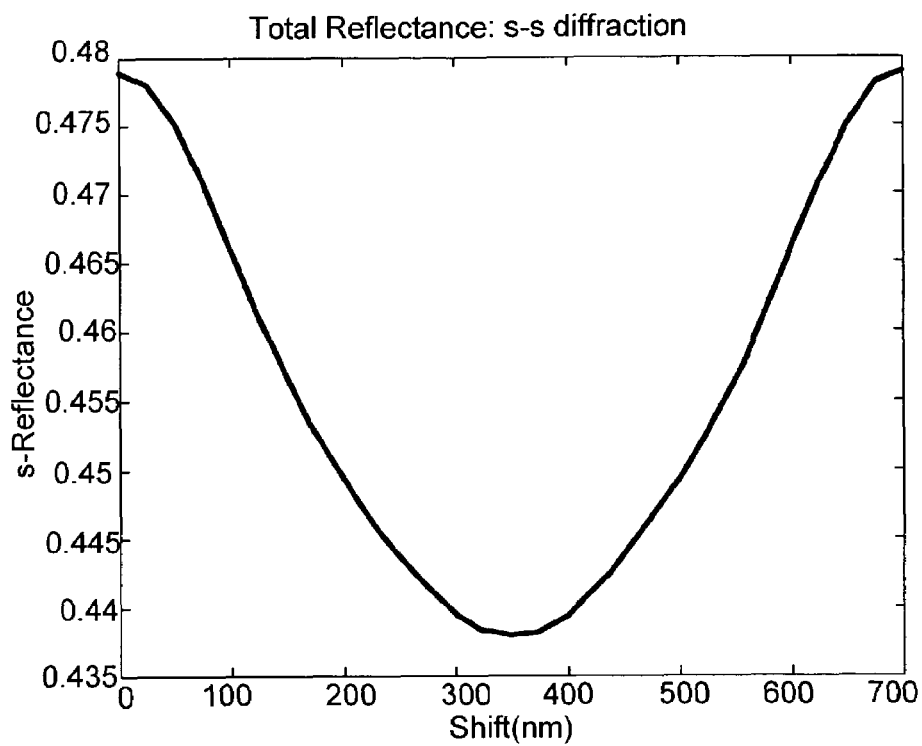

FIG. 18 is a graph showing the reflectance of p type polarized light a function of the shift between the top and bottom patterns, where the incident light is s polarized and light has an incident angle of 60 degrees. As can be seen, the resulting reflection has a clear periodic pattern. FIG. 19 is a graph showing the reflectance of p type polarized light as a function of shift, where the incident light is p polarized and the light has an incident angle of 60 degrees. FIG. 20 is a graph showing the reflectance of s type polarized light as a function of shift, where the incident light is s polarized and the light has an incident angle of 60 degrees.

Thus, as can be seen in FIGS. 17A and 17B, the intensity of the p type polarized light in the resulting beam increases as the misalignment between top and bottom periodic patterns is increased. The change in the intensity of the light is periodic as can be seen in FIGS. 18, 19, and 20. Accordingly, by monitoring the single polarization state (s or p) of the resulting beam as either the top periodic pattern 700a or the bottom periodic pattern 700b are moved, it may be determined when the top and bottom periodic patterns are aligned. As shown in FIG. 18, for cross polarization states, e.g., the incident beam is s type polarized and the p type polarization is monitored in the resulting beam, a minimum will indicate when the patterns are aligned or 90 degrees out of phase. Where the same polarization state is monitored as is incident, e.g., p type polarization is incident and monitored as shown in FIG. 19, maxima will indicate when the patterns are aligned or 90 degrees out of phase. Where s type polarization is incident and monitored, as shown in FIG. 20, maxima will indicate when the patterns are aligned.

Figure 21:
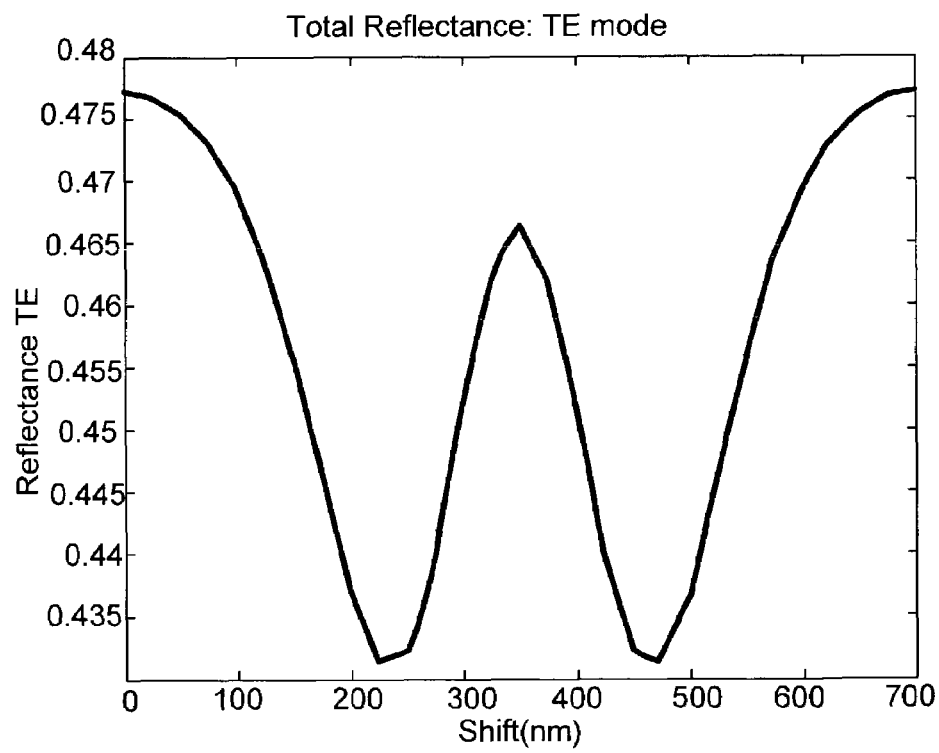
FIGS. 21 and 22 show graphs of reflected light as a function of shift between the top and bottom periodic patterns, where the light is normally incident on the alignment target.
Figure 22:
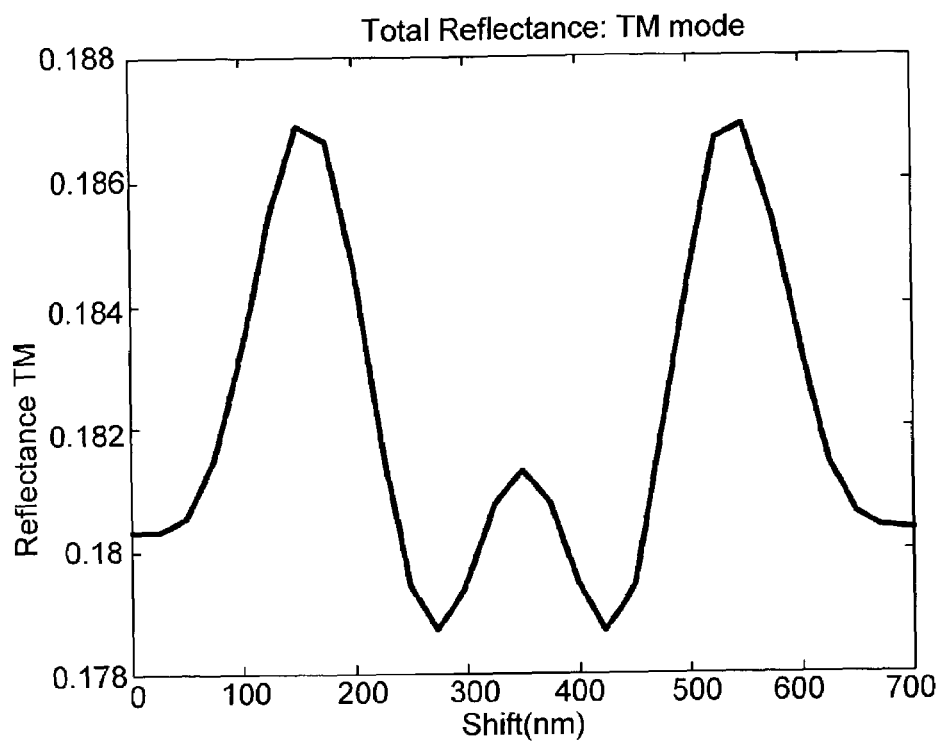

As discussed above, normally incident light may be used to monitor the misalignment between the top and bottom periodic patterns, e.g., using a normal incidence metrology device, such as that shown in FIG. 8A. FIGS. 21 and 22 show graphs of the reflectance of TE and TM mode light, respectively, as a function of shift between the top and bottom periodic patterns, where the incident light is in TE and TM mode, respectively, and is normal to the substrate. Similar to what is shown in FIGS. 18, 19, and 20, FIGS. 21 and 22 show that the resulting measurement of the TE and TM modes of the reflected light is periodic and, thus, can be used to determine when the periodic patterns are in alignment.

As described in reference to FIG. 10, additional alignment targets may be used as reference targets. One of the alignment targets has a designed in offset D. By comparing the measurement alignment target with the reference alignment target, as described in equations 1 and 2, the offset amount may be determined. Moreover, additional alignment targets may be used as described in the U.S. patent application entitled "Alignment Target with Designed in Offset" by Weidong Yang, Roger R. Lowe-Webb, and John D. Heaton, which is incorporated herein by reference.

Alternatively, the alignment target 700 can be self-referenced, by taking a measurement at a first location, moving either the top or bottom periodic pattern with respect to the other by a known distance D, and taking a second measurement. The first and second measurements may then be used along with distance D to determine the alignment error, as described in equations 1 and 2. Once the alignment error is determined, either the top or bottom periodic pattern is moved with respect to the other by the amount of the alignment error to minimize the error. If desired, a third measurement may be made. Because the alignment error is minimized, the intensity of the polarization state of the resulting beam should be approximately zero. However, if the intensity of the polarization state of the resulting beam is non-zero, the amount of the current alignment error may be determined by comparing the third measurement with the second measurement, as described in equations 1 and 2, where D is distance that the periodic patterns were previously moved to minimize the alignment error.

Figure 23:
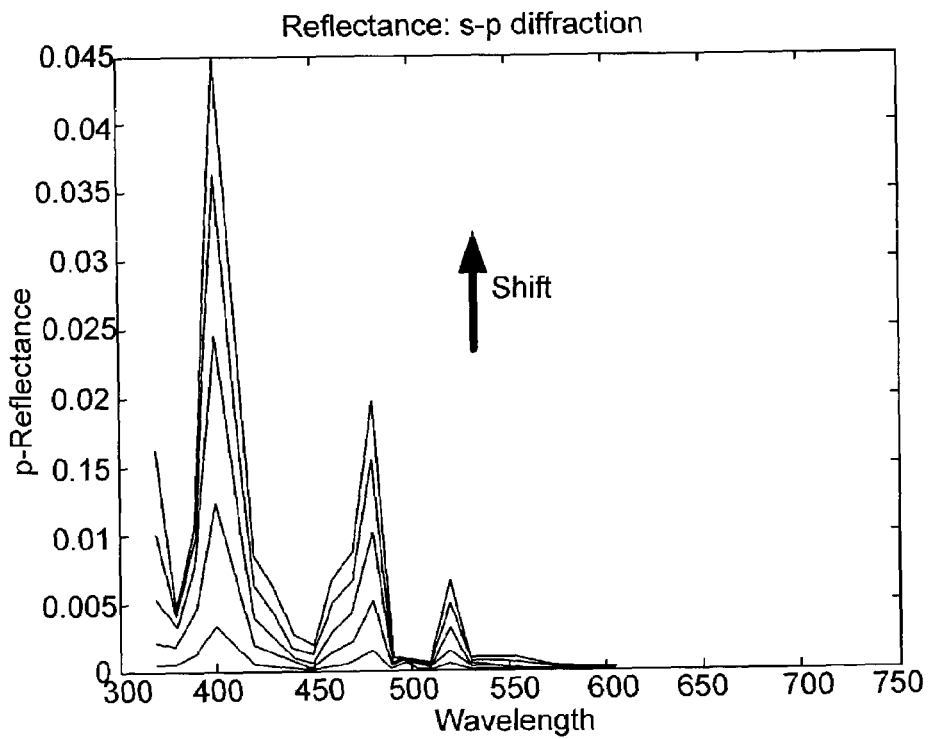
FIG. 23 shows a graph of the reflected light as a function wavelength and shift between the top and bottom periodic patterns.

As discussed above, it should also be understood, that the present invention may use a single wavelength, a plurality of discrete wavelengths, or a continuum of wavelengths. FIG. 23, for example, shows a graph of the reflected p type polarized with respect to wavelength, where the incident light is s type polarized. FIG. 23 shows a plurality of curves for different shifts between the top periodic pattern and bottom periodic pattern. As can be seen in FIG. 23, certain wavelengths, e.g., approximately 400 nm, are more responsive to overlay shifts than other wavelengths.

It should be understood that the determination of whether two elements are in alignment may be used advantageously with an alignment system, such as that shown in FIGS. 6 and 7, or with an encoder device, such as that described in "Encoder with Alignment Target", by Weidong Yang, Roger R. Lowe-Webb, and John D. Heaton which is incorporated herein by reference.

Figure 24:
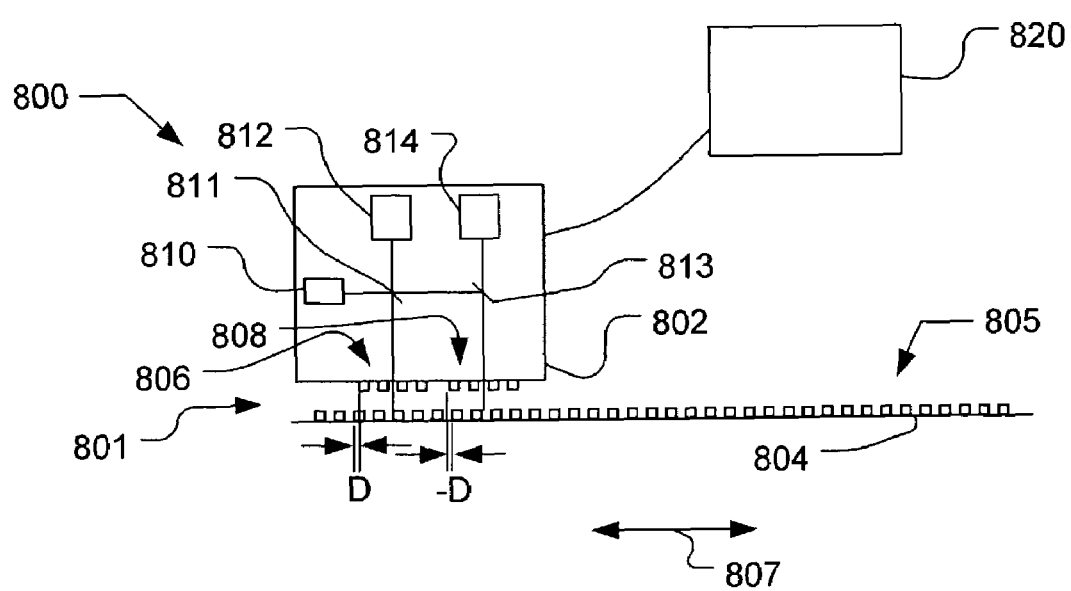
FIG. 24 shows one embodiment of an encoder that uses an alignment pattern, in accordance with the present invention.

FIG. 24 shows one embodiment of an encoder 800 that uses an alignment pattern 801, in accordance with the present invention. Encoder 800 includes a sensor head 802 and a scale 804. The scale 804 includes a continuous periodic pattern 805, such as a diffraction grating. In operation, the sensor head 802 and the scale 804 are movable with respect to each other, as indicated by arrow 807. One of the elements, e.g., the sensor head 802, moves, while the other element, e.g., the scale 804, is held stationary. Encoder 800 may be used as a linear encoder or as a rotary encoder.

In one embodiment, the sensor head 802 may have two or more measurement locations, each of which includes a periodic pattern 806 and 808. In another embodiment, only one measurement location is used. Sensor head 802 also includes a light source 810, which may be, e.g., a white LED source. If desired, an external light source may be used, in which case the light source may be coupled to the sensor head 802, e.g., by a fiber optic cable. Moreover, if desired, more than one light source may be used, e.g., one light source for each measurement location.

Sensor head 802 can operate in reflection mode or transmission mode. FIG. 24 illustrates sensor head 802 operating in reflection mode. As shown, beams splitters 811 and 813 direct the light from light source 802 towards the periodic patterns 806 and 808, respectively. The light passes through periodic patterns 806 and 808, and is reflected back by the periodic pattern 805 on the scale 804. The reflected light passes through beam splitters 811 and 813 and is received by detectors 812 and 814, respectively. Thus, the two measurement locations include both the periodic patterns 806 and 808 on the sensor head 802 and the periodic pattern 805 on the scale 804. Thus, it should be understood that periodic patterns 806 and 805 together will be sometimes referred to as measurement location 806, and likewise, periodic patterns 808 and 805 will be sometimes referred to as measurement location 808.

If desired, multiple light sources may be used in sensor head 802. Sensor head 802 may use a reflectometer type device to measure the measurement locations 806 and 808. The operation of reflectometers and similar devices is well known in the art. Moreover, if desired, sensor head 802 may operate in transmission mode. In transmission mode, the light is transmitted through periodic pattern 805 on scale 804, as opposed to being reflected, and is received by detectors on the other side of scale 804.

The detectors 812 and 814 detect the resulting light and convert the light into electrical signals that are received by processor 820 coupled to the sensor head 802.

Encoder 800 may use a single polarization state to monitor when the top and bottom periodic patterns are in alignment. By determining when the periodic patterns are in alignment, and by knowing the distance between the lines in the periodic patterns, the processor can determine the relative position between the sensor head 802 and the scale 804. The resolution of the encoder 800 can be further improved by interpolating the position of the sensor head 802 relative to the scale 804 based on a recorded measurement of the signal over one period.

Alternatively, the second measurement location 808 may be used in conjunction with the first measurement location 806 as discussed above.

Although the invention has been described with reference to particular embodiments, the description is only an example of the invention's application and should not be taken as a limitation. Various other adaptations and combinations of features of the embodiments disclosed are within the scope of the invention as defined by the following claims.

What is claimed is:

1. A method comprising:
   providing an alignment target on a first element and a second element, the alignment target having a first periodic pattern on said first element and a second periodic pattern on said second element;
   illuminating said first periodic pattern and said second periodic pattern of said alignment target with incident light having a first polarization state, said incident light interacts with said alignment target;
   detecting a given polarization state of the resulting light after interacting with said first periodic pattern and said second periodic pattern;
   determining the alignment of said first element with respect to said second element based on the detected light;
   moving said first element with respect to said second element when it is determined based on the detected light that said first element is not aligned with said second element.

2. The method of claim 1, wherein said given polarization state is said first polarization state.

3. The method of claim 1, wherein said given polarization state is a second polarization state, wherein said second polarization state is perpendicular to said first polarization state.

4. The method of claim 1, wherein said first polarization state is one of s type and p type polarization.

5. The method of claim 4, wherein said given polarization state is one of s type and p type polarization.

6. The method of claim 1, wherein said first polarization state is perpendicular to the direction of periodicity of at least one of said first periodic pattern and said second periodic pattern.

7. The method of claim 1, wherein at least one of said first periodic pattern and said second periodic patterns are diffraction gratings.

8. The method of claim 1, wherein at least one of said first periodic pattern and said second periodic patterns has periodicities in two directions.

9. The method of claim 1, wherein said incident light is non-normally incident on said alignment target and has an azimuthal angle that is perpendicular to the periodicity of said first periodic pattern and said second periodic pattern.

10. The method of claim 1, wherein said incident light is normally incident on said alignment target.

11. The method of claim 1, further comprising moving said first element with respect to said second element if the detected polarized resulting light does not have a minimal intensity.

12. A method comprising:
   providing an alignment target on a first element and a second element, the alignment target having a first periodic pattern on said first element and a second periodic pattern on said second element, said alignment target further includes a third periodic pattern on said first element and a fourth periodic pattern on said second element, said third periodic pattern and said fourth periodic pattern have a designed in offset of a known magnitude such that when said first element and second element are aligned, said third periodic pattern and said fourth periodic pattern are offset by said known magnitude;
   illuminating said first periodic pattern and said second periodic pattern of said alignment target with incident light having a first polarization state, said incident light interacts with said alignment target;
   detecting a given polarization state of the resulting light after interacting with said first periodic pattern and said second periodic pattern; and
   illuminating said third periodic pattern and said fourth periodic pattern of said alignment target with incident light having a first polarization state such that said incident light interacts with said third periodic pattern and said fourth periodic pattern;
   detecting a given polarization state of the resulting light after interacting with said third periodic pattern and said fourth periodic pattern; and
   determining the alignment of said first element with respect to said second element using both the detected light from said first periodic pattern and said second periodic pattern and the detected light from said third periodic pattern and said fourth periodic pattern.

13. The method of claim 12, further comprising:
   calculating the ratio of the intensity of said light from said first periodic pattern and said second periodic pattern and the difference between the intensity of said light from said first periodic pattern and said second periodic pattern and said detected light from said third periodic pattern and said fourth periodic pattern to determine the amount of alignment error between said first element and said second element.

14. The method of claim 1, wherein said first element is a sensor head and said second element is a scale for an encoder.

15. The method of claim 14, further comprising determining the relative position of said sensor head to said scale based on when said first element and said second element are aligned.

16. An apparatus for determining the alignment of a first element with a second element using an alignment target having a first periodic pattern on said first element and a second periodic pattern on said second element, said apparatus comprising:
   a light source for producing light having a first polarization state, said light is to be incident on said alignment target; and
   a polarizing element for polarizing said light after said light interacts with said alignment target;
   a detector for detecting the resulting polarized light after being polarized by said polarizing element; and
   a processor to determine when the alignment target is aligned based on the detected resulting polarized light; and
   a stage controlled by said processor, said stage moving said first element with respect to said second element to align said first element and said second element.

17. The apparatus of claim 16, wherein said first polarization state is one of perpendicular and parallel to the direction of periodicity of said first periodic pattern and said second periodic pattern.

18. The apparatus of claim 16, wherein said first element is a first layer on a substrate and said second element is a second layer on said substrate.

19. The apparatus of claim 18, wherein said first element is a first pattern produced on a first layer on a substrate and said second element is a second pattern produced on said first layer on said substrate.

20. The apparatus of claim 16, wherein said first polarization state is one of an s type and p type polarization state.

21. The apparatus of claim 20, wherein polarizing element polarizes said light after interacting with said alignment target to have one of an s type and p type polarization state.

22. The apparatus of claim 16, where said light source includes a first polarizer.

23. The apparatus of claim 22, wherein said polarizing element is said first polarizer.

24. The apparatus of claim 16, wherein said apparatus is an encoder.

* * * * *